US006015542A

United States Patent [19]
Kaminski et al.

[11] Patent Number: 6,015,542
[45] Date of Patent: *Jan. 18, 2000

[54] RADIOIMMUNOTHERAPY OF LYMPHOMA USING ANTI-CD20 ANTIBODIES

[75] Inventors: Mark S. Kaminski, Ann Arbor, Mich.; Gregory M. Butchko, Miami Lakes; Stephan D. Glenn, Davie, both of Fla.; Richard L. Wahl, Ann Arbor, Mich.

[73] Assignees: Coulter Pharmaceutical, Inc., South San Francisco, Calif.; The Regents of the University of Michigan, Ann Arbor, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/711,527

[22] Filed: Sep. 10, 1996

Related U.S. Application Data

[62] Division of application No. 08/121,282, Sep. 16, 1993, Pat. No. 5,595,721.

[51] Int. Cl.[7] .......................... A61K 51/10; A61K 39/395; C07K 16/00

[52] U.S. Cl. ..................... 424/1.49; 424/1.53; 424/174.1; 530/388.73; 530/391.3; 530/391.5

[58] Field of Search .................................. 424/1.49, 1.53, 424/144.1, 133.1, 1.69, 130.1, 179.1, 174.1, 172.1, 178.1; 530/391.3, 391.5, 388.73

[56] References Cited

U.S. PATENT DOCUMENTS

| | | | |
|---|---|---|---|
| 4,331,647 | 5/1982 | Goldenberg | 424/1.11 |
| 4,361,544 | 11/1982 | Goldenberg | 424/1.11 |
| 4,444,744 | 4/1984 | Goldenberg | 424/1.11 |
| 4,472,371 | 9/1984 | Burchiel et al. | |
| 4,921,690 | 5/1990 | Beatty et al. | 424/1.11 |
| 5,034,223 | 7/1991 | Abrams et al. | 424/85.8 |
| 5,120,525 | 6/1992 | Goldenberg | |
| 5,273,738 | 12/1993 | Matthews et al. | |
| 5,595,721 | 1/1997 | Kaminski et al. | 424/1.49 |
| 5,736,137 | 4/1998 | Anderson et al. | 424/133.1 |

FOREIGN PATENT DOCUMENTS

| | | |
|---|---|---|
| 0 669 836 B1 | 9/1995 | European Pat. Off. . |
| WO 94/11026 | 5/1994 | WIPO . |

OTHER PUBLICATIONS

Badger, C.C., et al., Experimental Radioimmunotherapy with I–131–Antibody Against a Differentiation Antigen, *J. Nuclear Med.*, 26(5):P67 (1985).

Badger, C.C., et al., Experimental Radioimmunotherapy of Murine Lymphoma with [131]I–Labeled Anti–T–Cell Antibodies, *Can. Res.*, 46:6223–6228 (1986).

Buchsbaum et al, "Therapy with Unlabeled and [131]I–Labeled Pan–B–Cell Monoclonal Antibodies in Nude Mice Bearing Raji Burkitt's Lymphoma Xenografts", *Cancer Research*, 52:6476–6481 (1992).

Buchsbaum et al., "Improved Delivery of Radiolabeled Anti–B1 Monoclonal Antibody to Raji Lymphoma Xenografts by Predosing with Unlabeled Anti–B1 Monoclonal Antibody", *Cancer Research*, 52:637–642 (1992).

Czuczman et al., "A Phase 1 Dose Escalation Trial of [131]Labeled Monoclonal antibody OKB7 in Patients with B Cell Lymphoma", Fourth Conference on Radioimmunodetection and Radioimmunotherapy of Cancer, Abstract #55 (Sep. 1992).

DeNardo et al., "Fractionated Radioimmunotherapy of B–Cell Malignancies with [131]I–Lym–1", *Cancer Research* (Suppl.), 50:1014s–1016s (Feb. 1990).

Eary et al., "Imaging and Treatment of B–Cell Lymphoma" *Journal of Nuclear Medicine*, 31(8):1257–1268 (Aug. 1990).

Eary et al., "Treatment of B–Cell Lymphoma with I–131 Labelled Murine Monoclonal Antibodies", *Proceedings of the 35th Annual Meeting, Scientific Papers*, 29(5) Abstract 70 (1988).

Ettinger et al., "Phase I–II Study of Isotopic Immunoglobulin Therapy for Primary Liver Cancer" *Cancer Treatment Reports*, 66(2):289–297 (Feb. 1982).

Goldenberg et al., "Targeting, Dosimetry, and Radioimmunotherapy of B–Cell Lymphomas With Iodine–131–Labeled LL2 Monoclonal Antibody", *Journal of Clinical Oncology*, 9(4):548–564 (Apr. 1991).

Kaminski et al., "Radioimmunotherapy of B–Cell Lymphoma with [$^{131}$I]Anti–B1 (Anti–CD20) Antibody", *New England Journal of Medicine*, 329:459–465 (Aug. 1993).

Kaminski et al., "Initial Clininal Radioimmunotherapy Results with 131–I–Anti–B1 (Anti CD20) Refractory B–Cell Lymphoma", Fourth Conference on Radioimmunodetection and Radioimmunotherapy of Cancer, Abstract #57 (Sep. 1992).

Kaminski et al., "131–I Anti–B1: Initial Clinical Evaluation in B–Cell Lymphoma", Third Conference on Radioimmunodetection and Radioimmunotherapy of Cancer, Abstract No. 144 (Nov. 1990).

Letvin et al., "Use of Radiolabeled Monoclonal Anti–B1 Antibody for B Lymphocyte Imaging in Rhesus Monkeys", *Nucl. Med. Biol.*, 14(2):99–105 (1987).

(List continued on next page.)

*Primary Examiner*—S. Mark Clardy
*Assistant Examiner*—Michael G. Hartley
*Attorney, Agent, or Firm*—Cooley Godward LLP

[57] ABSTRACT

Methods for the treatment of lymphoma by administration of a B cell-specific antibody are described. The invention encompasses providing to a patient both unlabeled antibodies and antibodies labeled with a radioisotope. A principal advantage of the method is that tumor responses can be obtained in a radiometric dose range that does not require hematopoietic stem cell replacement as an adjunct therapy also described is a composition useful in the treatment of lymphoma.

12 Claims, 7 Drawing Sheets

OTHER PUBLICATIONS

Macklis et al., "Induction of Programmed Cell Death in Malignant Lymphomas After Radioimmunotherapy", *Fourth Conference on Radioimmunodetection and Radioimmunotherapy of Cancer*, Abstract #39 (Sep. 1992).

Macklis et al., "Cell Cycle Alterations, Apoptosis, and Response to Low–Dose–Rate Radioimmunotherapy in Lymphoma Cells" *Int. J. Radiation Oncology Biol. Phys.*, 27:643–650 (1993).

Macklis et al., "Radiobiologic Basis of Lymphoma Radio–Immunotherapy", *Radiation Oncology Biol. Phys.*, vol. 24, Supplement 1, p. 184, Abstract #101 (1992).

Order, "Monoclonal Antibodies: Potential Role in Radiation Therapy and Oncology", *Int. J. Radiation Oncology Biol. Phys.*, 8(7):1193–1201 (1982).

Order et al., "Phase I–II Study of Radiolabeled Antibody Integrated in the Treatment of Primary Hepatic Malignancies", *Int. J. Radiation Oncology Biol. Phys.*, 6:703–710 (1980).

Parker et al., "Radioimmunotherapy of Human B–Cell Lymphoma with $^{90}$Y–Conjugated Antiidiotype Monoclonal Antibody", *Cancer Research*, (Suppl.) 50:1022s–1028s (Feb. 1990).

Press et al., "Treatment of Refractory Non–Hodgkin's Lymphoma With Radiolabeled MB–1 (Anti–CD37) Antibody", *Journal of Clinical Oncology*, 7(8):1027–1038 (Aug. 1989).

Press et al., "Monoclonal Antibody 1F5 (Anti–CD20) Serotherapy of Human B Cell Lymphomas", *Blood*, 69:584–591 (1987).

Press et al., "Radiolabeled Antibody (RAb) Therapy of Relapsed B Cell Lymphomas", *Lymphom*, Abstract #1077 (Apr. 1992).

Stashenko et al., "Characterization of a Human B Lymphocyte–Specific Antigen", *Journal of Immunology*, 125(4):1678–1685 (Oct. 1980).

Weinstein et al., "Monoclonal Antibodies in the Lymphatics: Toward the Diagnosis and Therapy of Tumor Metastases", *Science*, 218:1334–1337 (Dec. 1982).

"Immunomedics Reports on Lymphoma Imaging and Therapy Progress at Cancer Conference", New Jersey, *Cancer Research Weekly* (1993).

RADIOIMMUNOTHERAPY OF LYMPHOMA USING ANTI-CD20 ANTIBODIES

CROSS REFERENCE TO RELATED APPLICATIONS

This application is a Divisional of U.S. Ser. No. 08/121,582, filed Sep. 16, 1993, now U.S. Pat. No. 5,545,721.

ACKNOWLEDGEMENT

This invention was made with U.S. Government support under Grant Nos. CA42768 and CA56794 awarded by the National Institutes of Health. The U.S. Government has certain rights in this invention.

FIELD OF THE INVENTION

The invention relates to therapy of lymphoma using antibodies directed to an antigen present on the surface of the lymphoma cells. The antibody demonstrates a therapeutic effect when administered per se, however, greatly enhanced therapeutic effect is seen when the antibody is labeled with a toxic substance, e.g. radioactively Labeled. The amount of radioactivity used to label the antibody is preferably low enough that toxicity to bone marrow and other tissues is avoided, yet high enough to effect complete remission of the lymphoma.

DESCRIPTION OF RELATED ART

Although significant advances have been made in the treatment of non-Hodgkin's lymphoma over the past two decades, a curative regimen for patients with low-grade B cell lymphomas has yet to be developed. In addition, durable remission in patients treated with various regimens for refractory intermediate- and high-grade lymphomas have been relatively rare (1). Recent attempts utilizing supralethal chemotherapy combined with radiotherapy followed by bone marrow transplantation have resulted in an approximately 20% long term disease-free survival rate (2). However, most patients treated in this manner die of lymphoma or treatment related complications. Therefore, new strategies for the treatment of non-Hodgkin's lymphomas are needed. These strategies should have as their goal the maximization of therapeutic effect coupled with the minimization of toxicity.

One approach involves the use of monoclonal antibodies which recognize tumor-associated antigens as a means of targeting drugs or radioisotopes to tumor cells. This approach is particularly attractive in the case of non-Hodgkin's lymphomas as the tumor cells of these lymphomas display a variety of tumor-restricted antigens on their cell surfaces which would be available for targeting (3).

The rationale for utilizing such an approach is further supported by the observation that monoclonal antibodies by themselves can exhibit antitumor effects in vivo. Of all the malignancies that have been treated with monoclonal antibodies to date, the lymphomas have yielded the most dramatic results. In particular, significant tumor regressions have been reported in patients treated with monoclonal anti-idiotype antibodies (4,5). Most of the tumor responses, however, have been incomplete and of relatively short duration. The practical problem of generating anti-idiotype antibodies specific for each individual patient's idiotype and the emergence of idiotypic variants during anti-idiotype therapy (6) restricts the utility of such an approach.

In light of these findings, it is worth considering whether less restricted antigens on lymphoid tumor cells might be appropriate targets for therapy. In general, anti-tumor effects of antibodies against such antigens have only been modest. Patients with chronic lymphocytic leukemia (CLL) and cutaneous T-cell lymphomas, for instance, have been treated with the T101 antibody which hinds a 65 Kd glycoprotein present on malignant and some normal T-cells (7). Transient reductions in circulating malignant cells in CLL, patients and temporary improvements in skin lesions in cutaneous T-cell lymphoma patients, have been demonstrated (8–11) Recently, a number of murine monoclonal antibodies have been developed which recognize antigenic sites on both malignant and normal human B cells (12–19). These pan-B-cell antibodies have been useful in classifying lymphomas and in defining the ontogeny and biology of normal B cells. Therapeuticall these antibodies have principally been used in ex vivo purging of autologous bone marrow of malignant cells prior to bone marrow transplantation (20–22). The limited experience with these antibodies as therapeutic agents in vivo has indicated only modest activity (22, 23).

Because of the limited efficacy of unmodified antibodies in general, recent attention has focused on the use of antibodies conjugated to cytotoxic agents. Among the cytotoxic agents which might be considered, radioisotopes are especially attractive, as lymphomas are especially sensitive to the effects of radiation. Moreover, such radiolabeled antibodies may be of considerable utility in terms of diagnostic imaging of tumor involved sites. Imaging trials have been carried out using $^{111}$In and $^{131}$I conjugated to T101 antibody, for example, in patients with CLL and cutaneous T-cell lymphoma (24). Intravenous administration of $^{111}$In-labeled T101 was shown to be capable of detecting tumors as small as 0.5 cm in diameter. These studies also demonstrated that isotope localization to tumor could be achieved despite the presence of target antigen on normal as well as malignant cells.

The therapeutic potential of radiolabeled antibodies in lymphoma has recently come under investigation. Badger et al., using a murine T-cell lymphoma model, have demonstrated that a monoclonal antibody against the Thy 1.1 differentiation antigen labeled with $^{131}$I was superior to unmodified antibody in its therapeutic effect (25) The dose limiting toxicity in these experiments was that of bone marrow suppression. Rosen et al, have reported their results using $^{131}$I-labeled T-101 antibody in the imaging and therapy of 6 patients with cutaneous T-cell lymphoma in which significant responses of disease lasting 3 weeks to 3 months were observed (26). As in the murine model of T-cell lymphoma, myelosuppression was again seen as the dose limiting toxicity in these patients.

Since greater than 75% of all non-Hodgkin's lymphomas are of B cell lineage, we and others have begun to investigate the use of pan-B-cell monoclonal antibodies labeled with radioisotopes in preclinical and clinical studies. We have been able to demonstrate, for instance, using a nude mouse model of xenografted human B cell lymphomas, that radiolabeled pan-B-cell antibodies can be specifically targeted to B cell tumors in vivo (27) and that these radiolabeled antibodies can have therapeutic effects. DeNardo et al. have reported their experience with $^{13}$I-labeled Lym-1 antibody (28). Lym-1 is an IgG2a antibody which recognizes a cell surface antigen of 31–35 Kd, which appears to be an HLA-Dr antigen, and reacts with normal and malignant B cells (29).

Recently, we performed a study using the pan-B-cell antibody MB-1 labeled with radioiodine as a radioimmunodiagnostic and therapeutic agent. MB-1 is an IgG1 anti-CD37 monoclonal antibody, which binds to B cells bearing the 40 Kd cell surface protein CD37. MB-1 binds to almost no pre-B cells (30). This antibody has been found to also react with granulocytes, platelets, and T cells, but the magnitude of this binding is less than the binding to B lymphocytes. No binding has been observed with tissues from stomach, thyroid, kidney, skin, peripheral nerve, heart, and cervix. In a study, twelve patients with refractory B cell lymphoma were evaluated for the biodistribution of $^{131}$I-labeled MB-1, its imaging potential, toxicity, and therapeutic effect. Successful imaging of tumors has been achieved in all but one of our patients, but not all known tumor sites were visualized in all patients. Significant clinical responses have been documented, although only one complete response and one partial response were achieved at the dose levels employed. Also, severe myelosuppression precluded further dose escalation.

Press et al. have reported their experience with $^{131}$I-MB-1 using higher radioactivity and protein doses than those we employed in our trial (31). Four patients have been treated with single doses of between 232 and 608 mCi of iodinated antibody combined with large doses of antibody (2.5–10 mg/kg total antibody) with provision for autologous bone marrow rescue. Each of these four patients obtained a complete tumor remission. Severe myelosuppression occurred in all patients, however, with two patients requiring reinfusion of previously stored autologous bone marrow. No other significant acute toxicity was seen. Two patients relapsed with lymphoma 4 and 6 months after achieving complete remission and the remaining two patients remain in continuous remission at 8 and 11 months.

It is presently unclear why a substantial number of patients will not receive radiation doses to all tumor sites which are significantly above those doses given to normal tissues using Lym-1 or MB-1. Whether this is due to the nature of the antibody being utilized, the stability of the radiolabel in vivo, the method of administration, the overall tumor burden within the host, or other factors related to the tumor or its vasculature remains to be determined. One factor which should be seriously considered is the cross-reactivities encountered with these two antibodies with either normal non-lymphoid tissues or other hematopcietic cells. The biodistribution patterns of antibodies with more restricted specificity for B cells might be more favorable in that nonspecific absorption in vivo might be reduced.

One antibody that is somewhat more specific for B cells is the antibody LL2. A clinical study of radioimmunotherapy of lymphoma using labeled LL2 has been reported, but the results were somewhat disappointing, in that of only one of the five patients assessed exhibited a complete response, two patients exhibited a partial response, two exhibited a minor or mixed response, and severe myelosuppression was encountered (63).

CD20 is an antigen that is a 35 kilodalton, non-glycosylated phosphoprotein found on the surface of greater than 90% of B cells from peripheral blood or lymphoid organs. The antigen is expressed on the surface of virtually all resting B cells maintained in culture, but is lost by approximately one-third of the population upon activation of the cells by protein A or exposure to Epstein-Barr Virus. This result has been interpreted to mean that CD20 is lost during terminal differentiation of B cells (74). The antigen bound by LL2 shows a similar distribution to CD20, but is distinguishable by virtue of a lower antigen density on the surface of B cells for LL2 than for CD20 (77).

The 1F5 antibody against CD20 has been previously used in studies of radioimmunotherapy of lymphoma (31). Again, the results of this study were disappointing, in that only partial regression of the lymphoma of the treated patient was observed.

Another anti-CD20 antibody is the antibody anti-B1 (hereafter referred to as B1). B1 is an IgG2a that immunoprecipitates a 35 Kd cell surface phosphoprotein (CD20) expressed by normal B cells in various stages of differentiation, follicular and diffuse B cell lymphomas, and various lymphoid leukemias (32). No reactivity of this antibody has been demonstrated with granulocytes, platelets, thymus tissue, or T cells.

A significant amount of information is now available regarding the CD20 antigen which B1 recognizes. It is apparently expressed early in pre-B cell development just before the expression of cytoplasmic $\mu$ heavy chains and persists until plasma cell differentiation. The binding of B1 to the extracellular portion of the CD20 antigen generates a transmembrane signal which can inhibit the cell's entry into the S/G2+M stages after mitogen stimulation and also blocks differentiation into antibody-secreting cells (33–36). Antagonistic effects on B cell activation have also been observed with B1 binding and these differences may be due to differences in the state of activation of these cells before signal generation (37,38). Of interest are data using this antibody in nude mice bearing B cell lymphoma xenografts (39) and imaging performed in Rhesus monkeys using $^{131}$I-B1 in which the B cell rich spleen could be readily visualized by gamma camera scanning without need for image intensification or background subtraction techniques (36). The predominant use of B1, however, has been in the ex vivo purging of bone marrow prior to autologous bone marrow transplantation in patients with refractory leukemia and lymphoma (40). These studies have shown that marrow reconstitution is unaffected by the B1 antibody. Thus, B1 is an attractive antibody for use radioimmunodiagnoistically and radioimmunotherapeutically.

CD19 is another antigen that is expressed on the surface of cells of the B lineage. Like CD20, CD19 is found on cells throughout differentiation of the lineage from the stem cell stage up to a point just prior to terminal differentiation into plasma cells (74). Unlike CD20, however, antibody binding to CD19 causes internalization of the CD19 antigen. CD19 antigen is identified by the HD237-CD19 antibody (also B4 or the antibody of the B4–89B line, "B4" hereinafter) (92), among others. The CD19 antigen is present on % 4–8 of peripheral blood mononuclear cells and on greater than 90 percent of B cells isolated from peripheral blood, spleen, lymph node or tonsil. CD19 is not detected on peripheral blood T cells, monocytes or granulocytes. Virtually all non-T cell acute lymphoblastic leukemias (ALL), B cell CLL and B cell lymphomas express CD19 detectable by the antibody B4 (16, 94).

Additional antibodies which recognize differentiation stage-specific antigens expressed by cells of the B cell lineage have been identified. Among these are the B2 antibody, directed against the CD21 antigen, B3 antibody directed against the CD22 antigen and the J5 antigen, directed against the CD10 antigen (also called CALLA) (see FIG. 4). The reactivity of B4 with various tumor types is described above. B2 antibody reacts with resting B cells of all lymphoid types and is lost upon activation of the resting B cell. It can be used to identify heterogeneity in B cell CLL and lymphoma. B3 antibody marks all Hairy Cell leukemias. The CD22 antigen identified by B3 is found in the cytoplasm of virtually all B cell leukemias and lymphomas. The CALLA antigen identified by J5 is found on 80% of non-T cell ALLs and a significant portion of B and T cell lymphomas and some T cell leukemias. Of significance to the present invention, CALLA and CD19 are not expressed by greater than %95 of human bone marrow samples examined (83).

ABBREVIATIONS

The following abbreviations are used in this text:

cGy, centigrays; 1 cGy is approximately 1 rad; C R
CR, complete remission
CT, computed Tomography;
DTPA, diethylenetriaminepentaacetic acid;
EDTA, ethylenediaminetetraacetic acid;
MX-DTPA, metal chelate-diethylentraminepentaacetic acid;
mCi, millicurie, 1 mCi=$2.2 \times 10^9$ decays per minute;
PR, partial remission;
PD, progressive disease;
RIC, radioimmunoconjugate;
RIS, radioimmunoscintigraphy;
RIT, radioimmunotherapy;

SUMMARY OF THE INVENTION

The present invention provides compositions and articles of manufacture which comprise the antibody B1, which binds specifically to the CD20 antigen of B cells, and also provides methods for immunotherapy of lymphoma which employ the B1 antibody. In particular, the articles of manufacture comprise the B1 antibody and printed matter which indicates that the antibody is to be employed in diagnostic imaging and/or immunotherapeutic methods. Compositions of the present invention comprise radioactively labelled B1 antibody and pharmaceutically acceptable carriers, diluents and the like. The methods employing B1 antibody encompass several embodiments.

One method for using the B1 antibody comprises administering radiolabeled B1 in a single dose designed to deliver a high amount of radioactivity. In such a method, it is contemplated that a radiometric dose of greater than 200 cGy is delivered to the whole body of the patient. In this "high-dose" method, bone marrow transplantation, or some other means of reconstituting hematopoietic function in the patient, is required.

In a second method using B1 antibody, a therapeutic dose of radiolabeled B1 antibody is administered, however, the radiometric dose received by the patient is limited to a level that toxicity to bone marrow is not significant and reconstitution of hematopoietic function, by bone marrow transplantation or other means, is not required. A range of dose effective in this method is one which delivers between 25 and 200 cGy, preferably 25 to 150 cGy to the whole body of the patient.

A third method using B1 antibody comprises administering to a patient a large amount of an unlabelled antibody, which can be B1 but can also be other antibodies, prior to administration of a therapeutic dose of labelled B1 antibody. This therapeutic dose can be made to deliver a radiometric dose of 5 to 500 cGy, preferably, 25 to 150 cGy, to the whole body of the patient.

A fourth method of using B1 antibody comprises administering a trace-labelled amount of B1 antibody, followed by imaging of the distribution of the B1 antibody in the patient. After imaging, a therapeutic regime of radiolabeled B1 is administered, designed to deliver a radiometric dose of 25 to 500 cGy, preferably 25 to 150 cGy, to the whole body of the patient.

The doses described above are limits for single administrations. Such administrations may be repeated, thus the patient might receive a much higher total accumulated dose over the course of imaging and therapy. It is considered, due to the similarity of the expression of CD20 and CD19 antigen in the B cell lineage, that the methods of the present invention can be applied using an anti-CD19 antibody, preferably HD237-CD19 or B4, in the same manner as is described for an anti-CD20 antibody.

Also, the invention is not limited to the CD19 and CD20 antibodies. Rather, the invention encompasses the use of antibodies which are identify antigens associated with cells of the B cell lineage to treat cancers which are clonal from such cells. Examples of such antibodies are B2, B3, B4 (HD-237), and J5, in addition to B1. Examples of such cancers are ALL, CLL, Hairy Cell leukemia, and chronic myeloblastic leukemias in a blast crisis stage, in addition to lymphomas.

Furthermore, it should be noted that the therapeutic method of the present invention is amenable to repeated administration for treatment of chronic disease or relapse after a period of remission. Also, the imaging applications described herein can be applied as diagnostic methods in their own right. That is, for example, the presence and location of CD20 positive cells in a patient can be determined independently of any therapeutic intent.

BRIEF DESCRIPTION OF THE DRAWINGS

FIG. 1B is an anterior view of Patient 9 obtained 120 hours after trace-labeled antibody injection. Multiple tumors (arrows) can be seen, 2 to 6 cm in diameter involving the neck, the right axilla, and the iliac, inguinal and femoral regions. FIG. 1A is a posterior view of Patient 2 obtained 235 hours after trace-labeled antibody injection. There is distinct focal uptake (arrows) within the spleen consistent with intrasplenic tumor targeting. A CT scan of this patient also demonstrated low-attenuation lesions in the spleen consistent with involvement by lymphoma.

FIG. 2 shows tumor responses to $^{131}$I-labeled anti-B1 antibody.

DETAILED DESCRIPTION OF THE INVENTION

Figure 1A:
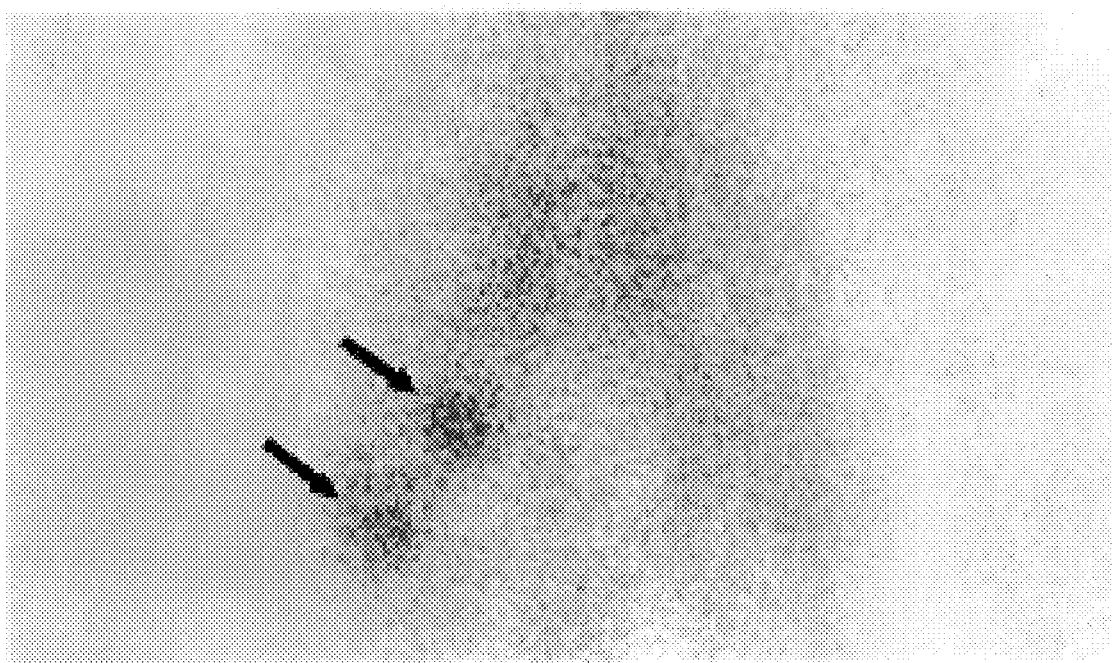
FIGS. 1A–1B shows gamma-camera images of patients with B cell lymphomas after injection of $^{131}$I-labeled anti-B1 antibody.

The principal problem of cancer chemotherapy is achieving good therapeutic indices for the compounds administered for the purpose of killing the tumor cells. In general, it has been found that tumoricidal drugs are also toxic to cells of normal tissue, and thus the side-effects of chemotherapy are often almost as devastating to the patient as the tumor burden itself. Typically, the approach used to achieve some degree of selectivity is to administer compounds which are preferentially taken up or preferentially toxic to rapidly dividing cells, when compared to their effect on growth arrested cells. This approach is limited by the fact that most, if not all, normal tissues contain compartments of dividing cells.

The advent of monoclonal antibody technology provided a new means of providing selectivity to chemotherapeutic agents. By conjugating the tumoricidal agent to an antibody directed against antigens present on tumor cells, but not present on normal cells, it was expected that selective killing of tumor cells could be achieved.

Many different conjugates have been created, using antibodies directed to a variety of cell-surface antigens and a variety of tumoricidal substances. To date the tumoricidal agents have principally been radioisotopes and various plant and bacterial toxins. However, while there are several reports of individual successes, the results of therapy using antibody conjugates has generally been disappointing. Remission rates have been low and not generally reproducible.

Lymphomas are tumors of the immune system. They present as both T cell- and as B cell-associated disease. Bone marrow, lymph nodes, spleen and circulating cells are all typically involved. Typically the initiating tumor cell is one of the blast cell types later in the lineage, rather than an early stem cell. This characteristic has allowed treatment protocols wherein bone marrow is removed from the patient and purged of tumor cells, using antibodies directed against antigens present on the tumor cell type, and stored. The patient is then given a toxic dose of radiation or chemotherapy and the purged bone marrow is then reinfused in order to repopulate the hematopoietic system of the patient.

The sorting of cells of the hematopoietic lineage, based upon surface-expressed antigens, is an established art, and several populations of hematopoietic cell types have been defined on that basis. In B cell lymphomas, antibody-targeted therapies have focussed on three particular antigens found on the surface of B cells, CD20, CD37 and the HLA-Dr antigens. As described above, therapeutic trials have been conducted using antibody conjugates recognizing each of these antigens. The method of the present invention employs an antibody directed against CD20, antibody B1, for the treatment of B cell lymphoma.

Antibody B1 is obtained from the Hall 299–15 cell line, which was first isolated at the Dana-Farber Cancer Institute. Coulter Clone® B1 can be purchased from the Coulter Corporation. Details of preparation of the antibody are provided below. The B1 antibody is of mouse origin. As such it can provoke a "human anti-mouse antibody" (HAMA) response in human recipients, although the frequency of this response is relatively low, especially in patients having B cell malignancies, due to the immunosuppressive character of the disease. Accordingly, use of an antibody comprising the B1 antigen-binding domain and a human Fc and hinge region is to be considered encompassed by the present invention, as well as alternative methods of "humanization" of the antibody, as such an antibody would be expected to be less likely to evoke a HAMA response, which can be limiting of retreatment of patients with the present method. However, HAMA responses occur much less frequently in persons with B cell malignancies due to the immunosuppressive character of the diseases. Furthermore, it is expected that it is advantageous to provide Fab, Fab' or F(ab')$_2$ fragments containing the antigen-binding portion of the B1 antibody as the B cell targeting moiety. Such antibody fragments might provide better diffusion characteristics in vivo, due to their smaller size, than the whole B1 antibody, in addition to also being less likely to evoke a HAMA response. While F(ab')$_2$ fragments of B1 itself are not stable, due to the IgG2a nature of the antibody, an IgG1 constant region variant of B1 could be produced which would form stable F(ab')$_2$ fragments. The means for engineering of antibodies by recombinant DNA and chemical modification methods are considered well-known in the art.

The B1 antigen (CD20) is present on approximately 9% of unfractionated peripheral blood mononuclear cells and on greater than 95% of normal B cells isolated from peripheral blood, lymphoid tissues, and bone marrow (12). It is also expressed on tumor cells isolated from 50% of patients with non-T cell acute lymphoblastic leukemias (ALL), greater than 95% of patients with B cell chronic lymphocytic leukemias (CLL), and greater than 90% with non-Hodgkin's B cell lymphomas. In contrast it is not reactive with resting or activated T cells, monocytes;, granulocytes, erythrocytes, or null cells, and tumors of T cell, myeloid, and erythroid origins. Functional studies demonstrated that the removal of the B1 reactive cells by cell sorting or by complement-mediated lysis eliminated all cells from peripheral blood and spleen capable of being induced by pokeweed mitogen to differentiate into immunoglobulin-secreting cells (80). The B1 antigen appears to be expressed on all stages of B cell differentiation from the pre-B cell and is lost just prior to the development of the plasma cell (80,81). The B1 antigen appears to be distinct from all previously described B cell determinants including conventional immunoglobulin isotypes, Ia-like antigens, and Fc and C3 receptors. The B1 antigen defines a cell surface non-glycosylated phosphoprotein of 35,000 daltons (82). The B1 antigen does not modulate from the surface of B1-positive cells after binding of B1 monoclonal antibody. The B1 antigen is usually found on 3–5% of normal human bone marrow cells (80). One to three percent of these cells contain intracytoplasmic immunoglobulin (83). Contaminating peripheral blood B cells in bone marrow account for the additional 1–2% staining and these cells express surface immunoglobulin. More recent studies have demonstrated that the B1 (CD20C) antigen appears in the mid-stages of human pre-B cell differentiation (83). The earliest B cell antigens, Ia and CALLA, precede the appearance of CD20 in pre-B cell ontogeny. All cytoplasmic $\mu$-positive pre-B cells express the B1 antigen.

B1 anti-CD20 is a murine IgG2a antibody and is capable of mediating in vitro lysis in the presence of rabbit complement. Mixing experiments with normal human bone marrow and tumor cell lines have demonstrated that anti-B1 can eradicate greater than 99% of tumor cells (84). Moreover, in these experiments there was no toxicity of either B1 anti-CD20 or the complement to early differentiated bone marrow stem cells as determined by the CFU-C, CFU-E, BFU-E and the mixed colony assay (85, 86).

B1 anti-CD20 did not decrease the growth of myeloid and erythroid precursors in a Dexter culture system (86). B1 anti-CD20 antibody, with its specificity for B cells, the lack of modulation of the CD20 antigen after B1 antibody binds, and its lack of toxicity to the myeloid pluripotent progenitor cells should bind to occult tumor cells of B cell origin in vivo and deliver a therapeutic radioisotope to the cell surface of recurrent NHL B cell tumor cells. Normal differentiated CD20-positive B cells will also bind B1 and be exposed to the therapeutic radioisotope, but the immature B cell precursor cells are not CD20-positive.

As noted above, the CD19 antigen is expressed in the B cell lineage in a fashion which is very similar to the CD20 antigen. Some of the properties of the CD19 antigen have been described hereinabove. Additional description of the CD19 antibody can be found in references 88–91. From this consideration, one of skill in the art would expect that the methods described in detail hereinbelow using the B1 antibody could also be applied using an antibody directed against the CD19 antigen, such as the anti-CD19 antibody, obtained from the cell line HD237-CD19 (Coulter designation MCB 88-8). This cell line was developed by Dörken et al. at the University of Heidelberg and is described in reference 92. A cell line of the Coulter Corporation, B4–89B, produces a similarly useful antibody.

Figure 4:
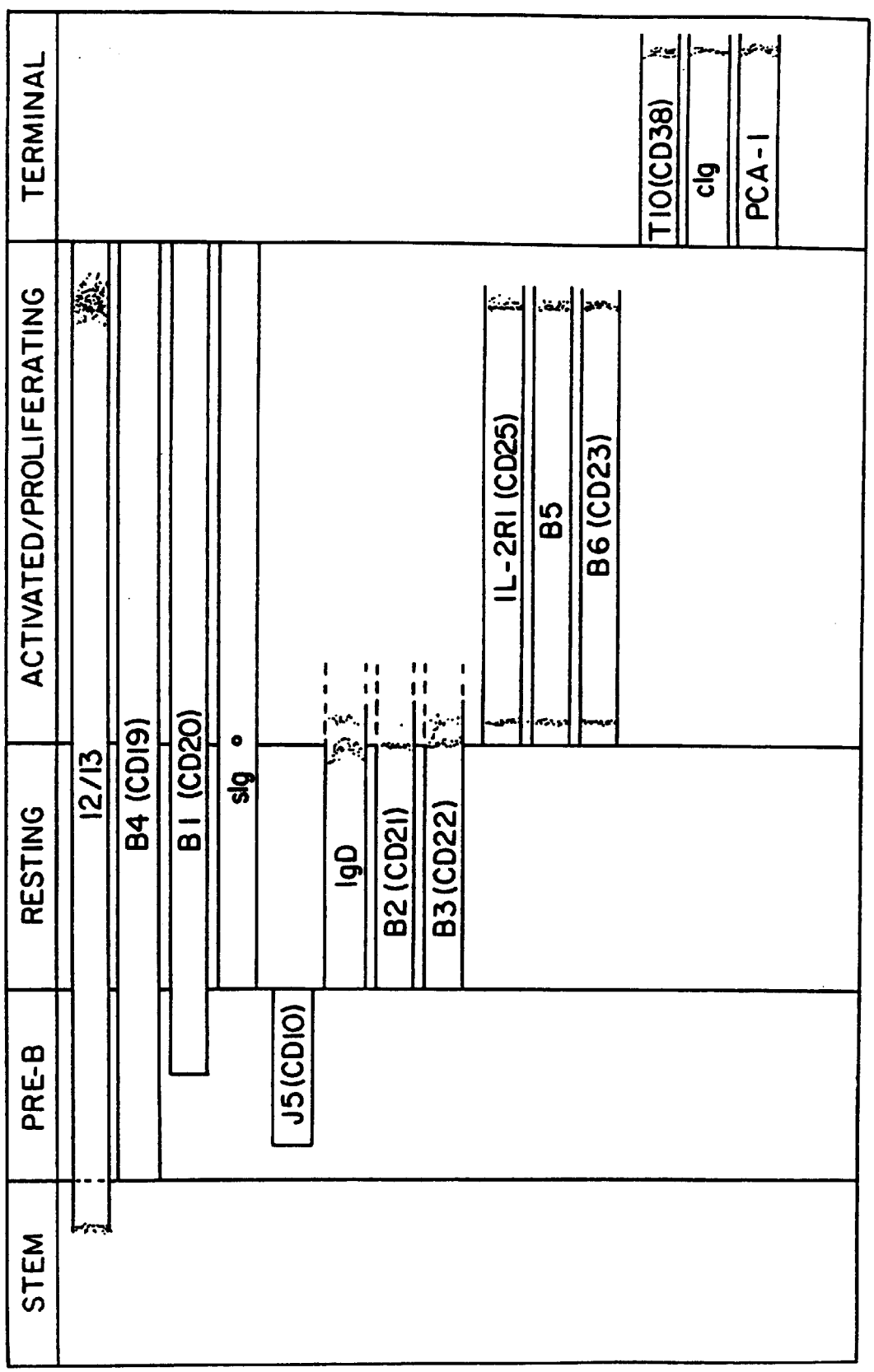
FIG. 4 shows a representation of the expression of various antigens during differentiation of the B cell lineage.

Additional neoplasms of B cell lineage which can be treated using the methods of the present invention are described above. Also described above, and in FIG. 4, are additional antigens (and antibodies against them) which are useful targets for imaging and therapy using the methods of the present invention. Each of the antibodies B2, B3, B4 and J5 can be purchased from the Coulter Corporation, Hialeah, Fla. For radiolabeling the antibody, there are several considerations for the method to be used. First, the radioisotope must be chosen, and then the means of attaching the radioisotope to the antibody must be selected. With respect to the choice of radioisotope, a general review of considerations is provided by Magerstadt (76). Principally one must consider the desired range of emission (affected by parameters including tissue type of the tumor, whether it is a solid or disseminated tumor and whether or not all tumor cells are expected to be antigen positive), the rate of energy release, the half-life of the isotope as compared to the infusion time and clearance rate, whether imaging or therapy is the aim of the labeled antibody administration, and the like. For imaging purposes according to the present invention, it is considered that labeling with $^{99}$Tc, $^{111}$In, $^{123}$I or $^{131}$I is preferable, with $^{111}$In or $^{131}$I labeling most preferred. For therapeutic purposes according to the present invention, it is considered that labeling with a $\beta^-$ emitter, such as $^{90}$Y or $^{131}$I is preferable. In some cases, labelling with an  emitter is appropriate. Additional isotopes that merit consideration for therapeutic or diagnostic uses are $^{186}$Re, $^{188}$Re, $^{153}$, $^{212}$Bi, $^{32}$P and radioactive isotopes of Lu.

In considering the means for attaching the radioisotope to the antibody, one must consider first the nature of the isotope. Iodine isotopes can be attached to the antibody by a number of methods which covalently attach the isotope directly to the protein. Chloramine T labeling (87) and iodogen labeling (45) are two commonly used methods of radioiodine labeling. For isotopes of metals, e.g. $^{90}$Y or $^{186}$Re, the isotope is typically attached by covalently attaching a chelating moiety to the antibody and then allowing the chelator to coordinate the metal. Such methods are described, for example, by Gansow et al., U.S. Pat. Nos. 4,831,175, 4,454,106 and 4,472,509, each of which is hereby incorporated in its entirety by reference.

It should be noted that antibodies labeled with iodine isotopes are subject to dehalogenation upon internalization into the target cell, while antibodies labeled by chelation are subject to radiation-induced scission of the chelator and to loss of radioisotope by dissociation of the coordination complex. In some instances, metal dissociated from the complex can be recomplexed, providing more rapid clearance of non-specifically localized isotope and therefore less toxicity to non-target tissues. For example, chelator compounds such as EDTA or DTPA can be infused into patients to provide a pool of chelator to bind released radiometal and facilitate excretion of free radioisotope in the urine. Also, it merits noting that free iodine, resulting from dehalogenation, and small, iodinated proteins are rapidly cleared from the body. This is advantageous in sparing normal tissue, including bone marrow, from radiotoxic effects.

Methods of administration are also reviewed by Magerstädt (76). For treatment of lymphoma, it is considered on the one hand that intravenous injection is a good method, as the thoroughness of the circulation in rapidly distributing the labeled antibody is advantageous, especially with respect to avoiding a high local concentration of the radiolabel at the injection site. Intravenous administration is subject to limitation by a "vascular barrier", comprising endothelial cells of the vasculature and the subendothelial matrix. Yet, it is also noted that this barrier is a larger problem for uptake of labeled antibody by solid tumors. Lymphomas have relatively high blood flow rates, contributing to effective antibody delivery. In the case administration for the treatment of lymphoma, consideration should also be given to intralymphatic routes of administration, such as subcutaneous or intramuscular injection, or by catherization of lymphatic vessels.

It is considered well-known to those of skill in the art how to formulate a proper composition of a labeled antibody for any of the aforementioned injection routes.

The timing of the administration can vary substantially. The entire dose can be provided in a single bolus. Alternatively, the dose can be provided by an extended infusion method or by repeated injections administered over a span of weeks. A preferable interval of time is six to twelve weeks between radioimmunotherapeutic doses. If low doses are used for radioimmunotherapy, the RIC could be administered at two week intervals. If the total therapeutic dose is fractionally delivered, it could be administered over a span of 2 to 4 days. Due to the lower dose infused, trace-labeled doses can be administered at short intervals; for clinical purposes, one to two week intervals are preferred.

The radiometric dosage to be applied can vary substantially. Lymphomas are known to be radiosensitive tumors. Furthermore, the anti-CD20 antibodies appear to have some effect upon lymphomas even when administered as unlabeled reagents. There is some evidence that this effect is mediated by "apoptosis", a reprogramming of the cellular metabolism that leads to lysis of the apoptotic cell (78). For immunodiagnostic imaging, trace-labeling of the antibody is used, typically 1–20 mg of antibody is labeled with about 1 to 35 mCi of radioisotope. The dose is somewhat dependent upon the isotope used for imaging; amounts in the higher end of the range, preferably 20 to 30 mCi, should be used with $^{99}$mTc and $^{123}$I; amounts in the lower end of the range, preferably 1–10 mCi, should be used with $^{131}$I and $^{111}$In. For imaging purposes about 1 to 30 mg of such trace-labeled antibody is given to the subject. For radioimmunotherapeutic purposes, the antibody is labeled to high specific activity. The specific activity obtained depends; upon the radioisotope used; for $^{111}$I, activity is typically 1 to 10 mCi/mg. The antibody is administered to the patient in sufficient amount that the whole body dose received is up to 1100 cGv, but preferably less than or equal to 500 cGy. The amount of antibody, including both labeled and unlabeled antibody, can range from 0.2 to 40 mg/kg of patient body weight.

An amount of radioactivity which would provide approximately 500 cGy to the whole body is estimated to be about 825 mCi of $^{131}$I. The amounts of radioactivity to be administered depend, in part, upon the isotope chosen. For therapeutic regimens using $^{131}$I, 5 to 1500 mCi might be employed, with preferable amounts being 5 to 800 mCi, 5 to 250 mCi being most preferable. For $^{90}$Y therapy, 1 to 200 mCi amounts of radioactivity are considered appropriate, with preferable amounts being 1 to 150 mCi, and 1 to 100 mCi being most preferred. The preferred means of estimating tissue doses from the amount of administered radioactivity is to perform an imaging or other pharmacokinetic regimen with a tracer dose, so as to obtain estimates of predicted dosimetry.

A "high-dose" protocol, in the range of 200 to 600 cGy (or higher) to the whole body, typically requires the support of a bone-marrow replacement protocol, as the bone-marrow is the tissue which limits the radiation dosage due to toxicity. A preferable dosage is in the range of 15 to 150 cGy to the whole body, the most preferable range being 40 to 120 cGy. Using such a "low-dose" protocol, toxicity to bone marrow is much lower and we have found complete remissions are achieved without the requirement of bone marrow replacement therapies.

Either or both the diagnostic and therapeutic administrations can be preceded by "pre-doses" of unlabeled antibody. The effects of pre-dosing upon both imaging and therapy have been found to vary from patient to patient. Generally, it is preferable to perform a series of diagnostic imaging administrations, using increasing pre-doses of unlabeled antibody. Then, the pre-dose providing the best ratio of tumor dose to whole body dose is used prior to the administration of the radioimmunotherapeutic dose.

Goldenberg et al. describe radioimmunodiagnostic imaging and radioimmunotherapy of solid tumors (carcinomas) using an anti-carcinoembryonic antigen antibody. Many aspects of the materials and methods described by them in U.S. Pat. Nos. 4,348,376 and 4,460,559, hereby incorporated in their entirety by reference, can be applied as well to the present invention, which is directed to the diagnosis and therapy of lymphoma, a more disseminated tumor. Additional description of methods for estimating the radiometric dose received by a patient are provided in reference 79.

The present invention also embodies articles of manufacture which comprises written material describing the use of an anti-CD20 antibody, or other antibody directed to an antigen associated with cells of the B cell lineage, in a radioimmunodiagnostic and/or radioimmunotherapeutic protocol. The written material can be applied directly to a container (such as by applying a label directly to a vial containing the antibody). Alternatively, holding the antibody can be placed in a second container, such as a box, and the written material, in the form of a packaging insert, can be placed in the second container together with the first container holding the antibody.

The written portion of the article of manufacture should describe indications for prescribing the antibody. Such indications would be presentation of lymphoma at any site in the body. The written material should further describe that the anti-CD20 antibody, or other antibody directed to an antigen associated with cells of the B cell lineage, is useful for the treatment of lymphoma or other neoplasm clonally derived from a cell of B cell lineage, indicated as set forth above. In a preferred embodiment of this aspect of the invention, the written material will describe B1, B2, B3, B4 or J5 as the antibody to be used in the treatment. In a most preferred embodiment, the written material will describe that B1 is used in the treatment of lymphoma. In other preferred embodiments, the written material will describe that the antibody is labeled with a $\beta^-$ emitting radionuclide, preferably $^{131}$I$_1$, $^{186}$Re, $^{188}$Re or $^{90}$Y$_1$. Still further, it can be described in the written material that the appropriate radiometric dose to be administered for an immunodiagnostic scanning is provided by 1 to 35 mCi of radioisotope, while the appropriate dose for therapeutic administration should be below 150 cGy to the whole body if bone marrow replacement support cannot be provided, but can be as high as 600 cGy to the whole body if bone marrow replacement support is provided. The doses for particular isotopes, especially as set forth hereinbelow, might also be described.

The written material would preferably be provided in the form required by the Food and Drug Administration for a package insert for a prescription drug. The written material would indicate that the antibody would be prescribed for use in patients having a diagnosis of B cell lymphoma and can be administered to patients presenting lymphoma in any site in the body. The written material would indicate that the antibody is useful as an initial or secondary treatment or in combination with other treatments. It would further describe that while the antibody delivers radiation preferentially to tumor sites, sometimes it will be observed that a normal organ will receive a radiometric dose higher than that delivered to the tumor.

Principal toxicities would be described as: myelosuppression, perhaps requiring bone marrow or stem cell reinfusion adjunct therapy, and fever, chills and/or hypotension upon infusion, hives and other typical allergic reactions. It would further be described in the written material that when symptoms such as fever or chills or other indications of allergic reactions are observed, HAMA should be tested. Additional side effects to be described are fatigue, usually mild and of a term of 4 to 6 weeks, and nausea, which is rare, but has been observed.

The written material should also describe that side effects presenting as allergic reactions might be related to the dose rate and can be ameliorated by slowing or stopping infusion of the antibody. Also, it should be described that fever and chills can be treated with Demerol™, Tylenol™, and/or an antihistamine, such as Benadryl™, and that hypotension responds well to fluid administration.

The written material should also describe that delivery of the antibody is preferably by slow intravenous infusion and might indicate a period for the infusion of one to 24 hours. Contraindications of the antibody are HAMA or previous allergic reaction and pregnancy. Furthermore, precautions should be described in the written material such as that it is recommended that patients be pre-medicated with acetomi-nophen (650 mg) and Benadryl™ (50 mg) prior to beginning the infusion. All patients receiving $^{131}$I-antibody should receive 2 drops of saturated potassium iodide solution (SSKI) three times daily for the period from 24 hours prior to the administration of the radiolabeled antibody until 14 days after the last administration. It should further be noted that serum should be monitored for HAMA response prior to the first administration, during therapy and follow-up.

The written material should also indicate that general radiologic and nuclear medicine precautions appropriate to the isotope used for labeling the antibody should be observed.

The following examples of the present invention are provided to illustrate the invention in more detail. The examples are to be taken as illustrative only, without limiting the scope of the invention.

EXAMPLE I

LOW-DOSE RADIOIMMUNOTHERAPY OF LYMPHOMA USING B1 ANTIBODY Methods

Anti-B1 Antibody Preparation and Iodination

The mouse IgG2a monoclonal antibody anti-B1 (anti-CD20) was provided by Coulter Corporation (Coulter Clone™ B1), Hialeah, Fla. It binds to a 35 kD cell-surface phosphoprotein expressed by greater than 95 percent of normal B cells isolated from peripheral lymphoid tissues, and bone marrow and greater than 90 percent of B cell lymphomas (5). It does not bind T cells, granulocytes, monocytes, erythrocytes, hematopoietic stem cells, nor any normal non-hematopoietic tissues (12).

The B1 antibody was isolated from serum-free hybridoma supernatants produced in cartridge-type bioreactors and purified by ion exchange chromatography. The resulting preparation was greater than 98 percent pure monomeric IgG, sterile, pyrogen-free, and free of adventitious viruses.

Radioiodination was performed using the iodogen method (45). After passage through an ion exchange column, which retains free iodine and allows passage of the labeled antibody, greater than 90 percent of $^{131}$I activity was protein-bound by thin layer chromatography. Alternatively, free iodine can be removed using a gel filtration column. The mean specific activities of trace-labeled and RIT-dose preparations were 0.83 and 8.8 mCi per mg, respectively. A rapid direct cell binding assay was performed before infusion using a one-hour incubation period to verify preservation of immunoreactivity as described previously (46). Lyophilized target B cells (Coulter Corporation) were reconstituted in distilled water and diluted in 2 percent bovine serum albumin in phosphate-buffered saline and incubated with radiolabeled antibody under conditions of antigen excess and in the presence or absence of excess unlabeled B1. For trace-labeled preparations, measured direct cell binding averaged 58 percent, and for RIT dose preparations, 49 percent. These represent minimum estimates of immunoreactivity not extrapolated to infinite antigen excess (47).

All radiolabeled antibody preparations were sterile-filtered and determined to be pyrogen-free by Limulus amebocyte lysate assay prior to injection. Antibody preparation and administration conformed to an approved Notice of Claimed Investigational Exemption for a New Drug.

Patient Selection

Adult patients with non-Hodgkin's lymphoma who had relapsed after or failed to respond to at least one prior chemotherapy regimen were eligible. Only patients whose tumor tissue was reactive with either B1 (by immunoperoxidase staining of cryopreserved tumor biopsies) or with L26 antibody (by staining of paraffin embedded tissue) were eligible. B1 and L26 both specifically bind the CD20 antigen (48). An iliac crest bone marrow biopsy was required to show to that less than 25 percent of the hematopoietic marrow elements were composed of lymphoma cells. Other eligibility requirements included lack of other treatment for at least four weeks, entry absolute granulocyte count greater than 1,500 per microliter and platelet count greater than 100,000 per microliter, normal hepatic and renal function, lack of other serious illnesses, Karnofsky performance status of at least 60, a life expectancy of at least 3 month, the presence of measurable disease, and the absence of serum human anti-mouse antibodies (HAMA) All patients provided written informed consent to the protocol which was approved by the Institutional Review Board of the University of Michigan.

Radiolabeled Antibody Administration

All patients were hospitalized and first received a trace-labeled dose (approximately 5 mCi, 15 mg) of $^{131}$I-B1 intravenously over 30 minutes. Biodistribution studies (described below) then followed. To evaluate the effect of unlabeled antibody predosing on radiolabeled antibody biodistribution and tumor targeting, a second trace-labeled dose was given approximately one week later which was immediately preceded by a 90-minute infusion of 135 mg of unlabeled B1. In some instances, a third trace-labeled dose was given one to two weeks later which was preceded by a 90-minute infusion of 685 mg of unlabeled antibody.

At least one week after the last trace-labeled dose, a higher radioactivity level RIT dose was administered. This RIT dose (15 mg) was given with the unlabeled antibody predose which resulted in the highest tumor/whole-body dose ratio in preceding trace-labeled dose biodistribution studies in that patient. The radioactivity dose (in mCi) administered for RIT was adjusted for each patient so that the patient would receive a specified whole-body radiation dose (cGy) predicted by the patient's trace-labeled dose biodistribution results. Sequential groups of at least three patients are scheduled to receive escalating whole-body doses, starting at 25 cGy and escalating by 10 cGy increments until a maximal tolerated dose not requiring bone marrow transplant support has been defined. Patients were eligible for retreatment after 8 weeks if they had not developed a HAMA response, had not experienced dose-limiting toxicity, had stable disease or tumor regression with measurable persistent disease, and if their blood counts, hepatic and renal function, and performance status were in a range that was originally required for protocol entry. Retreatment consisted of a trace-labeled dose (usually with the same unlabeled antibody predose used for the prior RIT dose) followed one week later by a RIT dose (also with the same unlabeled antibody predose) adjusted to deliver the same whole-body radiation dose delivered by the prior RIT dose.

Diphenhydramine (50 mg) and acetaminophen (650 mg) were given orally as premedication one hour prior to each infusion. Potassium iodide (SSKI) was given (two drops orally three times daily) beginning the day prior to the first antibody infusion and continuing until 14 days after the last infusion to inhibit thyroid uptake of radioiodine. Potassium perchlorate (200 mg three times daily for 7 days) was given in addition to SSKI to patients receiving RIT beginning the day of the RIT infusion. Patients were monitored for alterations in vital signs and for adverse reactions every 15 minutes during infusions. After RIT doses, patients were isolated in lead-shielded rooms until their whole-body radiation level was less than 30 mCi by ionization chamber measurements.

Dosimetric, Biodistribution, Pharmacokinetic, and Tumor Imaging Studies

Serial conjugate anterior and posterior whole-body and spot gamma camera scans, as well as NaI scintillation probe whole-body radioactivity counts, were obtained beginning one hour after trace-labeled dose administration and then daily for at least 5 days as previously described (49). Post RIT scanning began after a patient's whole-body radioactivity level was less than 30 mCi. Regions of interest outlines were drawn around normal organs, imaged tumors, and appropriate background regions by a computer. Time —activity curves (radioactivity/gram of tissue versus time) corresponding to these regions were then generated and fit by a least-squares regression program to derive an estimate of cumulative activity. Organ and tumor weights were derived from CT scan volumes when available, otherwise standard values for reference male or female organ masses were used (50). Dosimetric estimates were then made by the MIRD method (51–54).

Blood radioactivity clearance was determined from sequential blood samples drawn immediately through 120 hours post infusion and counted by gamma counter. Sera were also obtained for detection of immune complex formation (measured by high-performance liquid chromatography and C1q binding assays) within two hours following infusion. Urine was also collected at designated time intervals after infusion to measure the renal excretion rate.

Gamma scans were interpreted by a single experienced reader and compared with prestudy physical examinations, body CT scans, and other appropriate radiographic studies to determine tumor imaging sensitivity (49).

Toxicity Evaluations

Toxicity was scored according to the National Cancer Institutes Common Toxicity Criteria. Complete blood cell and platelet counts were obtained immediately after each infusion and then at 2, 4, 24, 72, and 120 hours post infusion. After discharge from the hospital, blood counts were obtained weekly for at least 8 weeks. Hepatic enzyme, renal, and electrolyte studies were performed at least twice during the week after an infusion and once every two weeks for the first two months after discharge. Serum complement levels (C3 and C4) were assayed within 2 hours following infusion. Peripheral blood immunophenotyping by flow cytometry was performed before and 24 hours after trace-labeled antibody infusions and one to two months post RIT. Direct staining of Ficoll-Hypaque separated mononuclear cells was performed with B1 and anti-CD19 antibodies for identifying B cells and with anti-CD3 antibodies for identifying T cells. Other antibodies used included anti-CD4, anti-CD8, anti-CD14, anti-CD45, and irrelevant subclass-matched antibodies.

HAMA responses were assessed from sera obtained prestudy, weekly until two months after the last antibody infusion, and monthly thereafter using a sandwich enzyme-linked immunosorbent assay described previously (49). Quantitative serum immunoglobulin levels and thyroid function tests were obtained prestudy, one month post RIT, and then several months post RIT.

Tumor Response Evaluations

Response was assessed during the tracer study interval prior to RIT, 4 to 6 weeks post RIT, and every two to three months thereafter. A complete remission (CR) was defined as complete disappearance of all detectable disease for a minimum of 4 weeks, a partial response (PR) as at least a 50 percent reduction in the sum of the products of the longest perpendicular diameters of all measurable lesions for a minimum of four weeks, and progressive disease (PD) as at least a 25 percent increase or the appearance of new lesions.

RESULTS

Ten patients entered on this study were initially evaluated and their characteristics are shown in Table 1. Half of the patients had low-grade lymphomas while the others had intermediate-grade lymphomas. At entry, three had high tumor burdens (greater than 500 g by CT and physical examination), two had low tumor burdens (less than 50 g), and five had intermediate tumor burdens (50–500 g). The patients were generally heavily pretreated with chemotherapy (mean number of regimens per patient=2.7). Half had chemotherapy—resistant disease, as defined by the inability to maintain a response lasting more than one month after the last administration of chemotherapy.

Gamma camera scans obtained after trace-labeled doses of anti-B1 demonstrated distinct tumor imaging of

TABLE 1

Clinical Characteristics of 10 Patients with B-Cell Lymphoma.

| PATIENT NO. | AGE (YR) | TUMOR HISTOLOGY* | TUMOR BURDEN (g) | MARROW INVOLVEMENT | PREVIOUS THERAPY† | CHEMOTHERAPY-RESISTANT DISEASE |
|---|---|---|---|---|---|---|
| 1 | 40 | DML | >500 | + | CHOP, Cyt-E-MTX, NovACOP-B | |
| 2 | 46 | FSC | 469 | + | CVP | + |
| 3 | 60 | DLC | | − | m-BACOD, DHAP, BEAC + ABMT | |
| 4 | 42 | F & DML | >500 | − | m-BACOD, BCNU-E-MTX-Pred, MINE, interferon | + |
| 5 | 56 | DLC | 236 | − | CHOP | + |
| 6 | 36 | FSC & LC | 60 | − | CVP, CHOP, BACOP, XRT | |
| 7 | 74 | DLC | <50 | − | CHOP, LEMP, Chlor-Pred, XRT | + |
| 8 | 70 | DSC | <50 | + | VACOP-B, DHAP | |

TABLE 1-continued

Clinical Characteristics of 10 Patients with B-Cell Lymphoma.

| PATIENT NO. | AGE (YR) | TUMOR HISTOLOGY* | TUMOR BURDEN (g) | MARROW INVOLVE-MENT | PREVIOUS THERAPY† | CHEMOTHERAPY-RESISTANT DISEASE |
|---|---|---|---|---|---|---|
| 9 | 59 | FML | 280 | – | Chlor, ProMACE/MOPP, interferon, chlorambucil, Cytox-Pred, CEPP, XRT, DICE | + |
| 10 | 57 | FML | 200 | – | CHOP, CVP, XRT | |

Figure 1B:
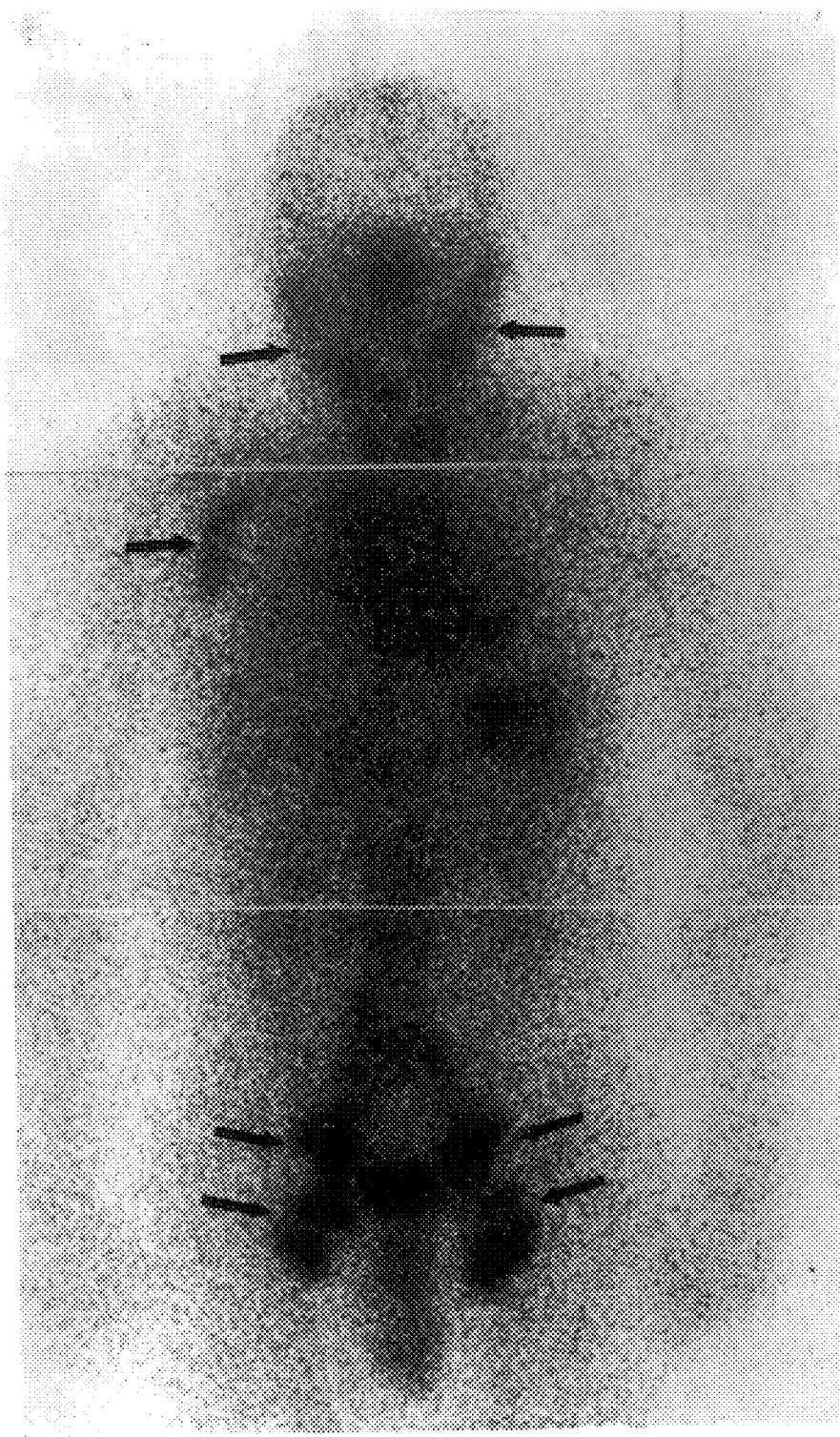

*DML denotes diffuse mixed large- and small-cell lymphoma; FSC, follicular small-cleaved cell lymphoma; DLC, diffuse large-cell lymphoma; F & DML, follicular and diffuse mixed large- and small-cell lymphoma; FSC & LC, follicular small-cleaved-cell lymphoma and follicular large-cell lymphoma in separate lesions; DSC, diffuse small-cleaved-cell lymphoma; and FML, follicular mixed large and small-cell lymphoma.
†CHOP denotes cyclophosphamide, doxorubicin, vincristine, and prednisone; Cyt-E-MTX, cyclophosphamide, etoposide, and methotrexate; NovACOP-B, mitoxantrone, doxorubicin, cyclophosphamide, vincristine, prednisone, and bleomycin; CVP, cyclophosphamide, vincristine, and prednisone; m-BACOD, methotrexate, bleomycin, doxorubicin, cyclophosphamide, vincristine, and dexamethasone; DHAP, dexamethasone, high-dose cytarabine, and cisplatin; BEAC + ABMT, carmustine, etoposide, cytarabine, and cyclophosphamide, with autologous bone marrow transplantation; BCNU-E-MTX-Pred, carmustine, etoposide, methotrexate, and prednisone; MINE, methotrexate, ifosfamide, mitoxantrone, and etoposide; BACOP, bleomycin, doxorubicin, cyclophosphamide, vincristine, and prednisone; XRT, external beam irradiation; LEMP, lomustine, etoposide, methotrexate, and prednisone; Chlor-Pred, chlorambucil and prednisone; VACOP-B, etoposide, doxorubicin, cyclophosphamide, vincristine, prednisone, and bleomycin; ProMACE/MOPP, methotrexate, doxorubicin, cyclophosphamide, etoposide, mechlorethamine, vincristine, procarbazine, and prednisone; Cytox-Pred, cyclophosphamide and prednisone; CEPP, cyclophosphamide, etoposide, procarbazine, and prednisone; and DICE, dexamethasone, ifosfamide, cisplatin, and etoposide.

all known disease sites larger Ehan 2 cm in all patients (30 of 30 known sites, range =1 to 9 per patient). Lesions from 1 cm to 15 cm in diameter could be detected, including intrasplenic tumors (FIG. 1).

Unlabeled B1 predosing was performed to assess the effect of such pre-dosing on the distribution of subsequently administered unlabeled antibody to tumors through partial or complete presaturation of non-specific binding sites and/or reservoirs of non-malignant B cells (especially those in the spleen). Predosing consistently prolonged blood and whole-body clearance of radioisotope compared to clearance of trace-labeled antibody without predosing, but its effect on radiolabeled antibody tumor targeting relative to normal tissues was variable. Of eight patients who received a 135 rg unlabeled antibody predose, two had a greater than 20 percent improvement in a tumor/whole-body dose ratio compared to a prior trace-labeled dose given without pre-dosing and three had no significant improvement. Three were unassessable due to either technical difficulties in dose assessment associated with the proximity of organs involved in excretion of free iodine or due to tumor volume decreases after trace-labeled antibody infusion. Two of two patients given subsequent trace-labeled doses preceded by a 635-mg unlabeled predose were also not assessable because of tumor responses, that is, decreases in tumor volumes, occurring after these infusions.

Table 2 shows that calculated radiation doses delivered to tumors by unlabeled antibody exceeded those to any normal organ in all but two of seven assessable patients. Up to 24.1 cGy per mCi (mean=10.6+/−2.76) could be delivered to tumor. Features unique to the two patients with poorer targeting which could account for suboptimal outcome were gross splenomegaly (750 g) in Patient 1 (the spleen could act as an "antigenic sink" for the labeled antibody) and a high degree of sclerosis in the tumor in Patient 5 (which might limit access of antibody to tumor cells).

Figure 2A:
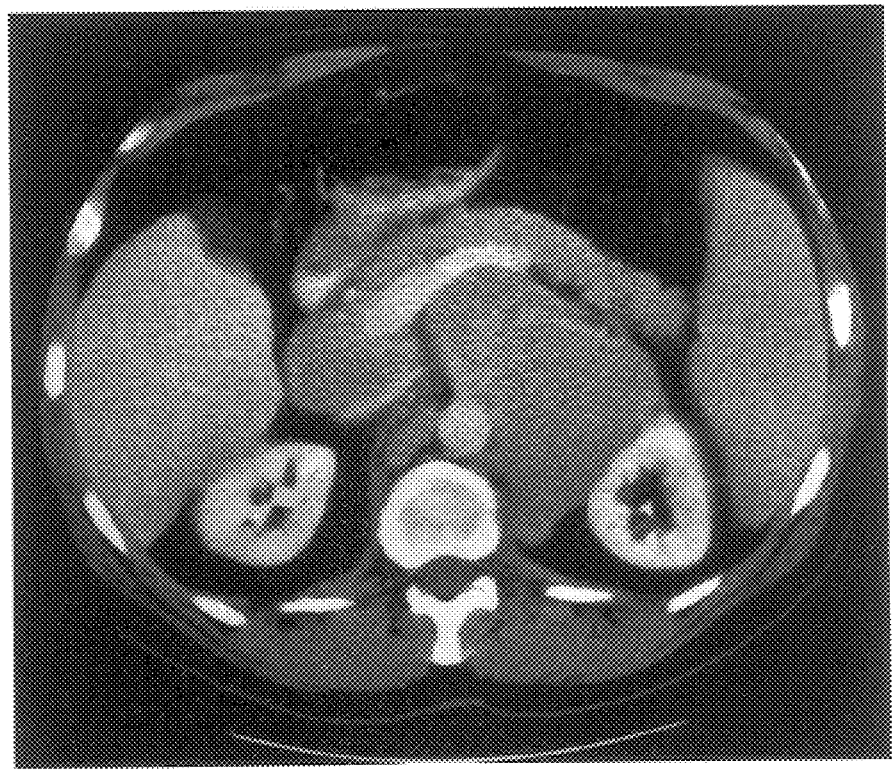
FIG. 2A shows abdominal CT images of Patient 4, showing a large chemotherapy resistant retroperitoneal mass before study entry.
Figure 2B:
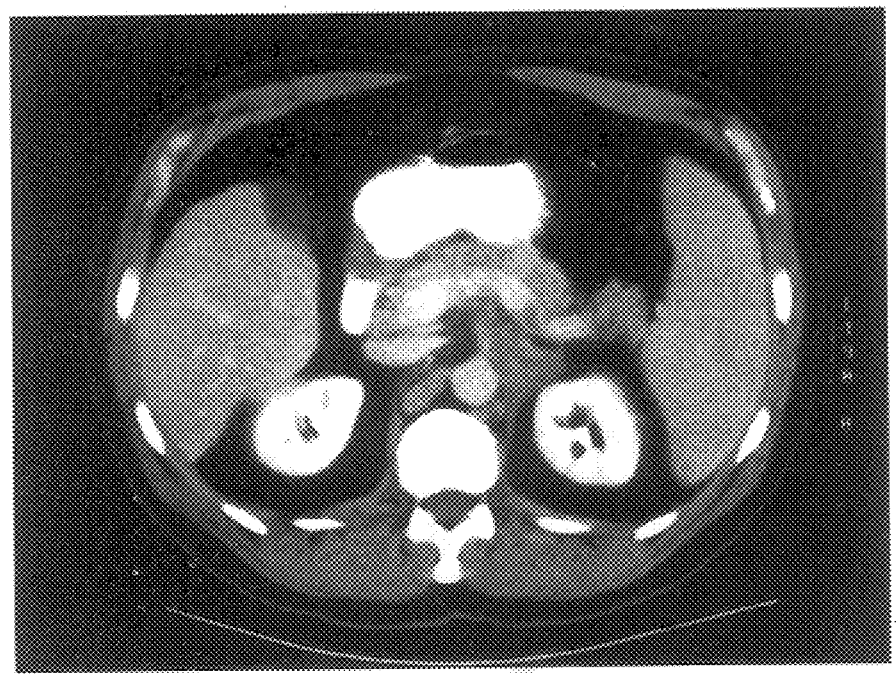
FIG. 2B shows regression of this mass after one round of radioimmunotherapy.
Figure 2C:
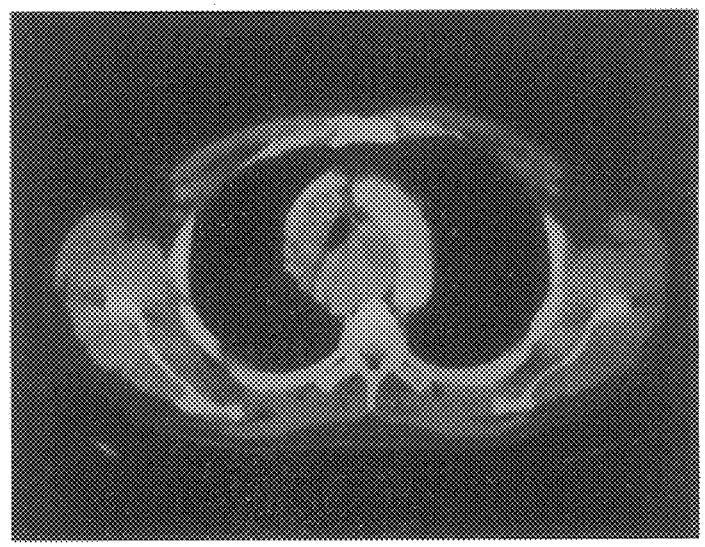
FIG. 2C shows thoracic CT images of Patient 2 before study entry.
Figure 2D:
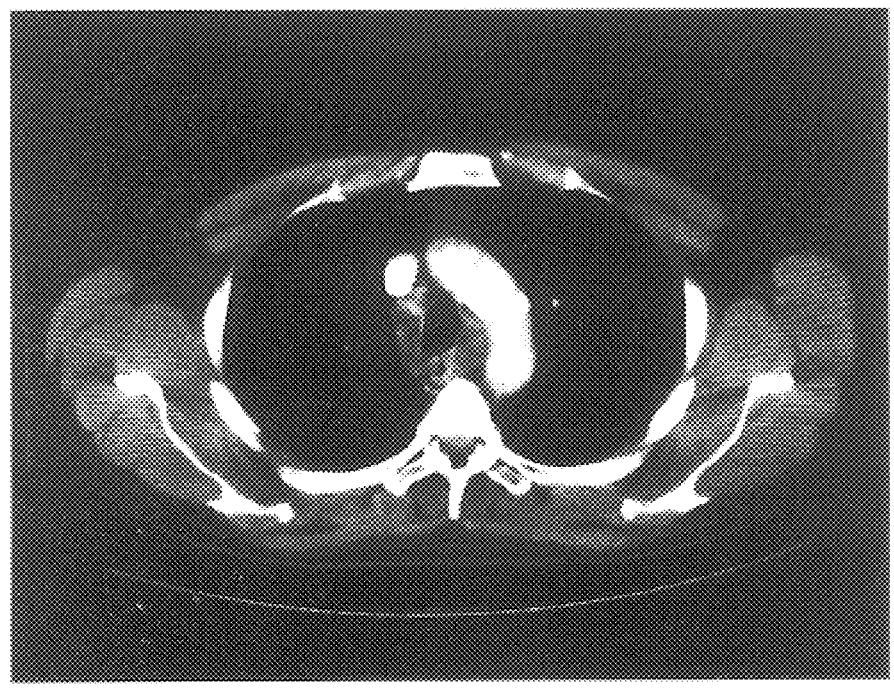
FIG. 2D shows CT imaging of the same section six weeks after one radioimmunotherapeutic dose of 45 mCi, showing the regression of chemotherapy-resistant mediastinal and peritracheal lymphadenopathy.

Nine patients received RIT doses and were evaluable for response and toxicity (Table 3) One patient did not receive an RIT dose because of rapid tumor progression and deterioration of physiologic status during tracer studies to the point of making the patient ineligible for protocol treatment. Four patients were treated twice (about two months between treatments). An estimated 25 to 45 cGy were delivered per dose to the whole body using 34 to 66 mCi per dose. Six of the nine patients had significant tumor responses, including four complete remissions (CRs) and two partial responses. Responses were observed in patients with extensive and/or bulky and chemotherapy-resistant disease (e.g. FIG. 2A and 2C). Three patients had responses (e.g. FIG. 2B and 2D) which began after trace-labeled doses even before RIT doses were given. All four patients

TABLE 2

Doses of Radiation Delivered by [$^{131}$I]Anti-B1 Antibody to Various Sites.

| PATIENT NO. | PRE-TREATMENT Dose (g) | SITE (cGy/mCi)* | | | | | | |
|---|---|---|---|---|---|---|---|---|
| | | TUMOR† | WHOLE BODY | BLOOD | KIDNEYS | LIVER | LUNGS | SPLEEN |
| 1 | 135 | 2.68 | 0.48 | 2.02 | 3.36 | 2.07 | 1.74 | 3.75 |
| 2 | 135 | 8.01 | 0.74 | 4.84 | 4.49 | 2.62 | 2.84 | 7.42‡ |

TABLE 2-continued

Doses of Radiation Delivered by [$^{131}$I]Anti-B1 Antibody to Various Sites.

| PATIENT NO. | PRE-TREATMENT Dose (g) | SITE (cGy/mCi)* | | | | | | |
|---|---|---|---|---|---|---|---|---|
| | | TUMOR† | WHOLE BODY | BLOOD | KIDNEYS | LIVER | LUNGS | SPLEEN |
| 4 | 0 | 8.77 | 0.55 | 3.03 | 6.14 | 2.45 | 2.33 | 2.01 |
| 5 | 0 | 3.72 | 0.88 | 4.48 | 6.24 | 2.49 | 2.38 | 7.31 |
| 6 | 135 | 24.1 | 0.76 | 3.87 | 4.43 | 2.39 | 2.23 | 4.49 |
| 9 | 0 | 12.1 | 0.74 | 4.44 | 4.36 | 2.23 | 1.72 | 8.12 |
| 10 | 135 | 14.6 | 0.73 | 5.76 | 7.24 | 3.12 | 4.38 | 3.47 |
| Mean ± SE | | 10.6 ± 2.76 | 0.69 ± 0.05 | 4.06 ± 0.46 | 5.18 ± 0.52 | 2.48 ± 0.13 | 2.52 ± 0.34 | 5.22 ± 0.89 |

*Values shown reflect the trace-labeled doses resulting in the highest delivered dose to tumor in each patient.
†Values shown are the maximal doses delivered to any of a patient's tumors.
ⁿCT scans showed multiple low-attenuation lesions in the spleen that were consistent with involvement by lymphoma.

TABLE 3

Responses to Radioimmunotherapy.

| PATIENT No. | WHOLE-BODY DOSE AND ACTIVITY ADMINISTERED | | ANTIBODY DOSE | | HEMATOLOGIC TOXICITY | TUMOR RESPONSE | PERIOD WITHOUT DISEASE PROGRESSION |
|---|---|---|---|---|---|---|---|
| | cGy | mCi | THERAPEUTIC DOSE mg | TOTAL DOSE* | | | mo |
| 1 | 25 | 66 | 150 | 315 | Grade 1 | Disease progression | |
| 2 | 25 | 45 | 15 | 180 | None | Partial response | 5 |
| | 25 | 34 | 15 | 30 | Grade 1 | | |
| 3 | Not treated | Not treated | | 15 | | | |
| 4 | 25 | 57 | 15 | 180 | Grade 1 | Complete remission† | 8 |
| | 25 | 37 | 15 | 30 | Grade 2 | | |
| 5 | 35 | 38 | 15 | 30 | Grade 1 | Disease progression | |
| 6 | 35 | 40 | 700 | 1565 | Grade 1 | Complete remission‡ | ≧11 |
| 7 | 35 | 41 | 150 | 315 | None | Disease progression | |
| | 35 | 40 | 15 | 30 | None | | |
| 8 | 35 | 40 | 150 | 315 | Grade 2 | Complete remission§ | ≧9 |
| 9 | 45 | 44 | 150 | 315 | None | Partial response¶ | ≧2 |
| | 45 | 44 | 150 | 300 | Not evaluated‖ | Mixed response** | |
| 10 | 45 | 61 | 150 | 1015 | None | Complete remission¶ | ≧8 |

*Includes tracer doses.
†A remnant soft-tissue abnormality was seen in the area of previous tumor involvement on CT scanning after the first radioimmunotherapeutic dose; it did not substantively change after the second radioimmunotherapeutic dose. This remnant abnormality was believed to be scar tissue, because when the patient relapsed after eight months in the right paracaval region and conventional external beam irradiation to the abdomen was given, no change occurred.
‡Complete remission was induced with tracer doses.
§This was a probable complete remissino in a patient with mediastinal and axillary adenopathy and bone marrow involvement before therapy and a solitary, small, non-paratrabecular lymphoid aggregate found in follow-up biopsy specimens of iliac-crest bone marrow.
¶Partial response was induced with tracer doses and further response by radioimmunotherapeutic doses.
‖Although grade 3 thrombocytopenia was observed one month after radioimmunotherapy, this patient had rapidly progressing disease in previously involved and uninvolved sites, necessitating intervention with other treatment. Because no bone marrow biopsy was performed before the managing physician began therapy, no distinction could be made between peripheral blood-platelet destruction, progressive infiltration of marrow by lymphoma, and marrow toxicity.
**See the Results section for details.

with CRs achieved this status after only one RIT dose. Second RIT doses resulted in a mixed response in one patient (definite regression in some tumors and progression in others), no further disease response in two, and no change in a residual radiographic abnormality in one. One CR lasted 8 months, and three CRs continue progression-free for 8+ to 11+ months. Minimal toxicity was observed in all of the fully evaluable patients. Most had either reversible Grade I myelosuppression (leukopenia and/or thrombocytopenia) occurring 4 to 7 weeks post RIT or no toxicity. One patient had a mild rigor and fever during an RIT dose infusion.

Peripheral blood flow cytometry revealed that CD20-positive B cells constituted 2 to 20 percent of circulating mononuclear cells at baseline in our patients. Most had decreases in the percentage of CD20-positive cells 24 hours after tracer infusions with three patients showing complete depletion of these cells. All patients recovered their CD20 cell counts to close to baseline generally one to three months after RIT and did not show any evidence of increased rates of infection. No significant changes in circulating CD3-positive T cells were observed. Also, no significant changes in serum immunoglobulin levels have been seen with continued follow-up, including five patients who had low levels prestudy. Only two patients developed HAMA responses 53 and 81 days after the first trace-labeled antibody infusion. No instances of hypothyroidism induced by thyroid irradiation have yet been observed.

DISCUSSION

A striking proportion (four of six) of our observed responses have been complete and durable. This, together with the observation that responses could be achieved with a relatively short course of treatment in patients with bulky and/or extensive disease and chemotherapy-resistant disease, attests to the utility of this treatment. Although the ultimate length of complete remission in some of our patents has yet to be determined, this therapy offers, at the very least, excellent palliation of disease in view of its lack of toxicity and the potential for repeated treatments if relapse should occur.

Several factors may account for the excellent results obtained so far in our current trial and for why they appear better than those of other trials. First, anti-B1antibody appears to be a superior tumor targeting agent. Indeed, the ability to clearly image all tumors larger than 2 cm and even tumor lesions within the spleen (an organ rich in normal B cells) suggests a potential diagnostic role for radiolabeled anti-B1. These results compare favorably with those using the LL2 antibody (63), are superior to those we previously obtained with MB-1 (56) and to those reported with the anti-CD21 antibody OKB7 (66). Also, our estimates of the radiation dose delivered to tumor in cGy per mCi by $^{131}$I-B1 (10.6+/−2.76) appears to be at least double that reported for other radiolabeled B cell antibodies (56,63,64,66). This may be, in part, because of the high degree of specificity of B1for B cells and its lack of crossreactivity with other cells. Also, in contrast to the antigens targeted by other studied antibodies, the CD20 antigen does not modulate (i.e., disappear from the cell surface via cytosolic internalization or cell surface membrane shedding) after antibody binding (12). Since internalization of radiolabeled antibody may result in dehalogenation of antibody and subsequent release of free iodine from the cell (67), the absence of such a mechanism may result in prolonged retention of intact radiolabeled antibody by the targeted cell. Notably, better tumor targeting appeared to translate into improved tumor responses in our patients. Those patients with relatively poorer targeting did not, in general, respond to treatment This may also indicate that the tumor responses observed were more likely due to antibody-targeted radiation rather than simply whole-body irradiation.

In one patient with gross splenomegaly (Patient 1) significant improvement with antibody predosing was seen. When no predose was given to this patient, radioactivity localized predominantly to the spleen and no tumor sites were detectable, but with a 135-mg predose, splenic uptake of radioisotope was much reduced and the patient's multiple tumor sites became detectable. This supports our hypothesis that unlabeled antibody predosing may help radiolabeled antibody to bypass an antigenic sink (such as the spleen) and allow its better access to tumor sites through competitive binding mechanisms between unlabeled and labeled antibody.

Another factor potentially accounting for our results is the low radiation dose-rate associated with this form of delivery of radiation to targeted tumor cells. Animal model data have suggested that low dose-rate irradiation may, in fact, be more therapeutically effective than instantaneous irradiation fractionally delivered by conventional external beam (68–70), but the radiobiologic basis for this is still unclear. Also, recent observations have indicated that low dose-rate irradiation can induce apoptosis in lymphoid cell lines and that antibody binding to cells (including B1 binding) can synergize with this mode of irradiation to induce this effect (71,72).

The antibody moiety of the $^{131}$I-B1 conjugate may also be partly responsible for antitumor effects. B1is capable of inducing antibody-dependent cellular cytolysis (73) and complement-dependent cytolysis (20), probably because its Fc portion is of the IgG2a subclass. Also, B1can directly induce apoptosis in certain human B cell lymphoma cell lines. We have recently studied B1 antitumor effects in vivo in a n human B cell xenograft nude mouse model and have found that under certain conditions unlabeled B1 can have comparable inhibitory effects on tumor growth to $^{131}$I-labeled anti-B1 (73). Our observation of tumor responses during tracer studies in our clinical trial also suggests an antitumor role of the B1 antibody moiety. The relatively high dose of unlabeled antibody administered in some patients may have contributed to these responses. Indeed, in two of three instances in which a response occurred during tracer studies, the response was only seen after the largest dose of antibody (700 mg) was administered (Patients 6 and 10). However, in these cases and those in which a response appeared to occur only after an RIT dose, a targeted radiation effect is also likely, especially since targeting of radioisotope was found to be so high in these cases and could result in the delivery to tumor of up to 120 cGy per tracer dose (Table 2).

Finally, it is certainly possible that at least six different anti-tumor mechanisms discussed above can be working in concert either additively or synergistically in this treatment including 1) antibody-targeted radiation, 2) low dose-rate irradiation and its incompletely understood effects, 3) whole-body irradiation, 4) antibody-dependent cellular cytolysis, 5) complement-dependent cytolysis, 6) and antibody-induced apoptosis.

EXAMPLE II

ADDITIONAL PATIENTS TREATED BY $^{131}$I B1 RADIOIMMUNOTHERAPY

Twelve additional patients were treated essentially as described in Example I, bringing the total number of patients to 22. The cumulative results of all 22 patients are summarized as follows:

All received between 1 and 3 trace-labeled doses intravenously (5 mCi labelling 15 mg of B1 antibody), spaced at weekly intervals. Trace-labeled doses were immediately preceded by either no pretreatment, pretreatment with 135 mg and pretreatment with 685 mg of unlabeled antibody. 16 of the patients received additional radioimmunotherapeutic doses, ranging from 34 to 93 mCi, preceded by that dose of unlabeled antibody that resulted in the best tumor imaging in the tracer study. Six patients were unable to receive radio-immunotherapeutic doses due either to disease progression resulting in physiologic deterioration (n=3) or due to development of a HAMA response (n=3).

Of the 22 patients, 15 exhibited a tumor response (CR or PR). Of the 16 patients receiving a radioimmunotherapeutic dose, 13 exhibited CR or PR. Eight of the patients who received a radioimmunotherapeutic dose exhibited CR. Of these 8 patients with CR, 2 have relapsed (8 and 13 months post-RIT) and the remaining 6 have remained disease free 16, 13, 8, 6, 3 and 2 months post-RIT, respectively. Tumor responses began during the tracer studies in 11 of the 22 patients, including 9 of the RIT patients, but the greatest proportion of the response, and the fastest rate of change, occurred following RIT. Toxicity has been minimal; maximum hematologic toxicity=grade 3 has been seen in only 3 patients, and that of short duration. The whole body dose range administered in patients to date has been between 25 and 65 cGy. The minimal toxicity observed indicates that escalation of doses is appropriate.

EXAMPLE III

$^{90}$Y RADIOIMMUNOCONJUGATES IN RADIOIMMUNOTHERAPY OF LYMPHOMA

General Considerations in Choosing Radioisotopes

For radioimmunoscintigraphy the radioisotopes of choice are characterized by relatively low energy gamma emissions with a physical half-life in the range of 6 hours to 8 days. A gamma emitter with principle emissions in the 0.1 to 0.2 Mev range is most ideal for scintigraphy, because the detection equipment is built with a focus on $^{99m}$Technetium which accounts for most of the Nuclear Medicine imaging procedures. The thickness of the detection device and collimator required for imaging with higher energy gamma emitters contribute to the fuzzy images obtained with high energy gamma emitters such as $^{131}$Iodine. An intact monoclonal antibody requires a period of hours to days to localize in tumor and a period of days for the blood pool and normal organ background to clear. Therefore, radioisotopes with very short half-lives are not very useful. Thus the initial dose in mCi must be very large for a short-lived radioisotope to have sufficient activity remaining at optimal imaging times. Radioiodines have been used extensively, but they suffer extensively from dehalogenation, especially upon internalizaion of the RIC into the target cell, and the lack of radioiodine with ideal characteristics ($^{123}$Iodine is probably the closest, but it suffers from great expense, uncertain supply of protein iodination grade material, and short half-life). Of the readily available radioisotopes for radioimmunoscintigraphy with an intact monoclonal antibody $^{111}$Indium is the current radioisotope of choice.

Gamma emitters are not suitable for radioimmunotherapy. α, β$^-$, and auger electron emitting radioisotopes have been proposed for radioimmunotherapeutic applications. Although α-emitting radioisotopes are an area of great research interest, there are no readily available α-emitting radioisotopes for which chelation chemistry has been developed that have isotopic half-life characteristics that match the pharmacokinetics of IgG monoclonal antibodies. The auger electron emitter $^{125}$I has been used for therapy purposes, but it suffers from dehalogenation and a long isotopic half-life (60 days). Several β$^-$-emitting isotopes appear to have promising characteristics for radioimmunotherapy. $^{186}$Re and $^{88}$Re are promising β$^-$-emitting radioisotopes that are under investigation, but their radioimmunoscintigraphy partner is suited for IgG fragments (Fab' & F(ab')$_2$), not IgG because of its short 6 hour half-life. A good β-emitting isotope for radioimmunotherapy using intact IgG is $^{90}$Y. It is a pure β$^-$-emitting isotope, so the unnecessary exposure by penetrating gamma emissions to hospital staff is minimized. This unfortunately does not allow $^{90}$Y to be used for radioimmunoscintigraphy for the purpose of developing predictive dosimetry with a sub-therapeutic dose of $^{90}$Y labeled antibody. The half-life of $^{90}$Y (2.6 days) is long enough that a significant percentage of the radiation dose will be delivered after tumor localization of the radiolabeled antibody has occurred and its half-life is short enough that the isotope will have decayed 97% in 13 days, so that hematological and immune system rescue via an autologous bone marrow transplant can be used in a reasonable time frame. A $^{90}$Y product suitable for high specific activity radiolabeling of chelated antibodies is available from the Amersham Corporation.

Because no yttrium isotope with characteristics for radioimmunoscintigraphy is readily available, $^{111}$In radiolabeled B1-MX-DTPA is used for radioimmunoscintigraphy and the dosimetry that would be obtained if 90Y were the radiolabel is estimated. $^{90}$Y radiolabeled B1-MX-DTPA is then used for radioimmunotherapy. We anticipate that there will be some inaccuracy in estimating the dosimetry of the $^{90}$Y to normal organs, especially the bone, because of the differing pharmacokinetic characteristics of the element iodine (which behaves somewhat like iron and is coordinated by the iron carrying protein transferrin) and yttrium (which behaves somewhat like calcium and concentrates in the mineral bone), but we expect that the effect of these differences in behaviors of these elements will be minimized in the dosimetry estimates, because bone marrow is the organ in which the dosimetry estimate will be most affected and autologous bone marrow transplantation can supplement the radioimmunotherapy regimen.

Dose escalation of $^{90}$Y labeled B1 can be performed in a cautious progression to minimize the chances of irreversible toxicities. The reproducibility of the correlation between the dosimetry predicted from $^{111}$In labeled El and toxicity and the effect of the $^{90}$Y labeled B1upon tumor tissue is an important consideration in use of $^{90}$Y labeled antibodies for therapy of cancers.

Characterization of B1Antigen and Anti-B1 Antibody

B1 antigen is expressed on all B cell cancers except for myelomas. B1antigen is absent from resting or activated T cells, erythrocytes, monocytes, Null cells, and granulocytes. B1 positive B cells occur in lymph nodes, bone marrow, spleen, and circulation. The results in transplants of autologous bone marrow purged with B and complement in non-Hodgkin's B cell lymphoma patients indicated that the B1 antigen is not expressed on the pre-B stem cell as there is normal reconstitution of the B cell population. Recent studies of the B1 antigen (CD20) indicate that B cells are the only cell type that express the mRNA for CD20 antigen.

We have studied tissue/organ specific binding of B1antibody beyond nonspecific scattered binding to tissue where nonspecific control antibodies also bind. The results of these studies are shown in Tables 4 through 6.

By virtue of its similar distribution in the B cell lineage, an antibody directed against the CD19 antigen is expected to be useful in the same manner as the B1 antibody. This is especially the case when $^{90}Y$ or $^{186}Re$ is the radioisotope used, since loss of the isotope upon internalization is not the problem that it is when a radiohalogen is used to label the antibody.

TABLE 4

B1 Reactivity with Frozen Normal Human Tissues Determined by Avidin-Biotin Immunoperoxidase Staining

| Frozen Adult Tissues | Reference #6771599 Number Positive/ Number Processed |
|---|---|
| Adrenal | 0/4 |
| Appendix | 0/3 |
| Breast | 0/1 |
| Cervix | 0/2 |
| Colon | 0/4 A |
| Esophagus | 0/3 |
| Fallopian Tube | 0/1 |
| Heart | 0/7 |
| Intestine | 0/2 |
| Kidney | 0/4 |
| Liver | 0/3 |
| Lung | 0/5 |
| Lymph Node | 2/4 |
| Nasal Polyp | 0/1 |
| Ovary | 0/4 |
| Pancreas | 0/2 B |
| Prostate | 0/9 |
| Spleen | 5/6 |
| Stomach | 0/7 |
| Thymus | 1/2 |
| Thyroid | 0/6 |
| Tonsil | 3/3 |
| Trachea | 0/3 |
| Uterus | 0/2 |

Key:
A: scattered glandular nonspecific artifact
B: scattered nonspecific activity in islets of Langerhans cells

TABLE 5

B1 Reactivity with Frozen Normal Fetal Tissues Determined by Avidin-Biotin Immunoperoxidase Staining

| Frozen Fetal Tissues | Reference #6771599 Number Positive/ Number Processed |
|---|---|
| Adrenal | 0/1 |
| Brain | 0/1 |
| Colon | 0/2 |
| Heart | 0/6 |
| Kidney | 0/6 |
| Liver | 0/6 |
| Lung | 0/6 |
| Pancreas | 0/1 |
| Small Intestine | 0/4 A |
| Smooth Muschle | 0/1 |
| Spleen | 5/5 |
| Stomach | 0/3 |
| Thymus | 0/1 |
| Untilical Cord | 0/3 |

Key:
A: scattered glandular nonspecific artifact

TABLE 6

B1 Reactivity with Frozen Lymphoma Tissues Determined by Avidin-Biotin Immunoperoxidase Staining

| Frozen Lymphoma Tissues | Reference #6771599 Number Positive/ Number Processed |
|---|---|
| B-Cell | 1/1 |
| Hodgkins | 0/1 |
| T-Cell | 0/1 |

We have observed no change in the specificity of 1 monoclonal antibody after conjugation with isothiocyanatobenzyl-methyl-DTPA and metalation with indium using standard conditions. Potential changes in the specificity of the B1 monoclonal antibody after labeling were addressed by comparing the immunohistochemical tissue specificity and immunofluorescence (flow cytometric and fluorescence microcopy) patterns of metalated (coordination complex with the stable isotope of In) B1-MX-DTPA versus untreated B1 monoclonal antibody (both the lot B1 that was parent to the BL-MX-DTPA and our QC backlot of B1). For this study 0.5 mL of nonradioactive $I_n$ at 0.2 ug/mL in 0.04 M HCl was added to 0.5 mL of 0.25 M sodium acetate (metal free). B1-MX-DTPA (2 mg) was added to the neutralized In solution and incubated for 20 min before adding 0.25 mL of 0.005 M calcium EDTA. The In-B1-MX-DTPA sample was then diluted in injectable saline.

For immunofluorescence analysis, the In-B1-MX-DTPA was tested side by side with its parent lot of B1 at doses of 20, 5, and 1.25 micrograms antibody per tube of human blood. The population of cells in normal human blood that bound B1were detected using fluoresceinisothiocyanate labeled goat anti-murine immunoglobulin (GAM-FITC) The whole blood samples examined by fluorescence microscopy showed no significant difference in the percentage of positive cells (3 to 5% of lymphocytes) and negative cells (0% of monocytes or granulocytes) or the intensity of staining (mean fluorescence channel of positive cells; 99 to 110 by flow cytometry).

To test that no new population of cells is recognized by the In-B1-MX-DTPA we performed a dual fluorescence labeling experiment using phycoerythrin conjugated B1 (PE-B1) and fluorescein-isothiocyanate labeled goat anti-murine immunoglobulin (GAM-FITC). Whole blood was reacted with an equimolar mixture of the PE-B1 and the In-B1-MX-DTPA parent lot. The cells were then washed of excess unbound murine antibody and reacted with GAM-FITC. In this experiment we would expect the fluorescent cells to fluoresce red (PE-B1) an green (GAM-FITC) if the PE-B1 and In-B1-MX-DTPA or parent lot B1 E bind to the same cells. Any cells that reacted only with In-B1-MX-DTPA but not with PE-B1would fluoresce "green" only and thus the conjugated B1 would be considered "damaged" since PE-B1 should bind to all cells bearing B1 antigen. The vast majority of the blood cells were negative (R-G-, 94 to 99% of cells). Five percent of the cells that were examined by microscopy and it of cells analyzed by flow cytometric analysis fluoresced both red (PE-B1) and green (GAM-FITC), indicating that B1 and In-B1-MX-DTPA recognize the same population of blood cells as PE-B1. The exception was that 1% of the cells examined microscopically appeared positive for PE-B1, but not GAM-FITC (R+G−) for the parent B1 lot. These results indicate that iridium labeled EL-MX-DTPA and B1 parent lot possesses the same specificity for circulating blood cells.

Another test of specificity of the metalated-B1-MX-DTPA was to study the immunohistochemical staining patterns of QC backlot, B1 parent lot, and In-B1-MX-DTPA using sections of frozen normal (not neoplastic) human tissue (both B cell negative tissues and B cell positive tissues). No significant differences in staining patterns of these three preparations of B1 are obvious upon examination of the slides. In normal tissue B1 is exclusively a membrane bound antigen. These tissue sections were considered positive if the outer cell membranes of any cells in the entire tissue section stain positive. Cytosolic binding was considered to be nonspecific in nature. Four adult control tissues (liver, prostate, heart, and uterus) and nine control fetal tissues (intestine, lung, liver, kidney, adrenal, heart, brain, thymus, and colon) were examined that should have been negative; all were negative with the three B1preparations tested, except for some cytosolic background binding. Most of the samples of the tissues that should be positive (tonsil, lymph node, and spleen) showed membrane staining typical of B1positive tissues with the three B1preparations tested. We conclude that there is no change in the tissue specificity of B1 that is detectable by these methods when it is conjugated to ITC-benzyl-DTPA and metalated (labeled) with In.

In non-cancerous tissue B1 appears exclusively as a membrane bound antigen. Tissue sections were considered positive if the outer cell membranes of any cells in the entire tissue section stain positive. Cytosolic binding of B1was considered to be nonspecific in nature. Four adult control tissues (liver, prostate, heart, and uterus) and nine control fetal tissues (intestine, lung, liver, kidney, adrenal, heart, brain, thymus, and colon) were examined that should have been negative, all were negative with the B1preparations tested, except for some cytosolic background binding. Most of the samples of the tissues that should be positive (tonsil, lymph node, and spleen) showed membrane staining typical of B1 positive tissues with the B1preparations tested.

Labeling of Antibody

We have found that B1 can be successfully conjugated with MX-DTPA and radiolabeled with $^{111}$In or $^{90}$Y (see below). By this radiolabeling method, the antigen reactive fraction for B1-MX-DTPA was 71±8(S.D.) for 27 determinations.

B1 is radiolabeled with $^{111}$In and $^{90}$Y, using a chelation labeling method originally developed at the National Cancer Institute and refined by Coulter Immunology. 1-p-Isothiocyanato-benzy-1-methyl-diethylenetriaminepentaacetic acid (ITC-MX) is used as the chelator. The synthesis of ITC-MX is a 6 step synthesis carried out by the Organic Chemistry Department of Coulter Immunology Division.

Figure 3A:
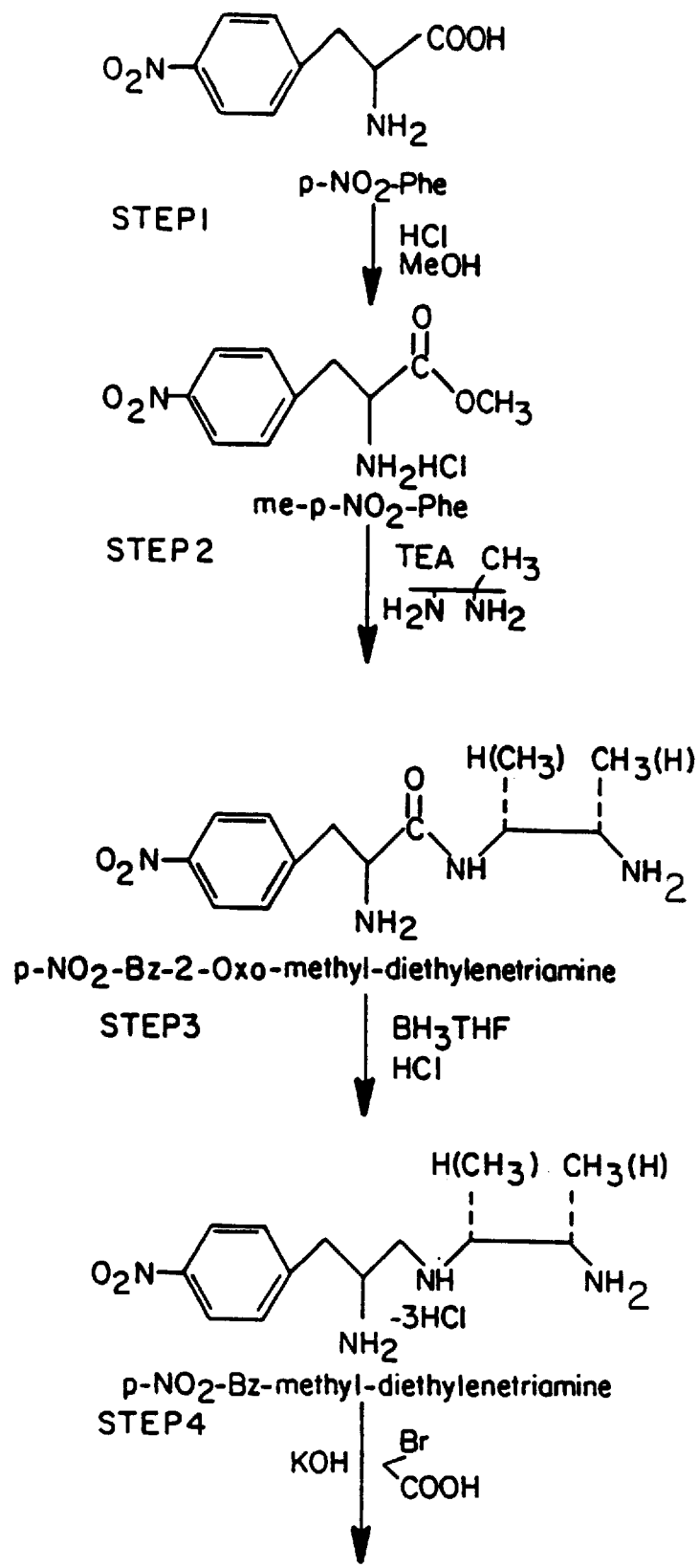
FIGS. 3A–3B show a synthetic pathway for (p-isothiocyanatobenzyl)methyl diethylenetriaminepentaacetic acid (mixture of 1-benzyl, 3-methyl and 1-benzyl, 4-methyl isomers). The pathway is modified from reference 93.
Figure 3B:
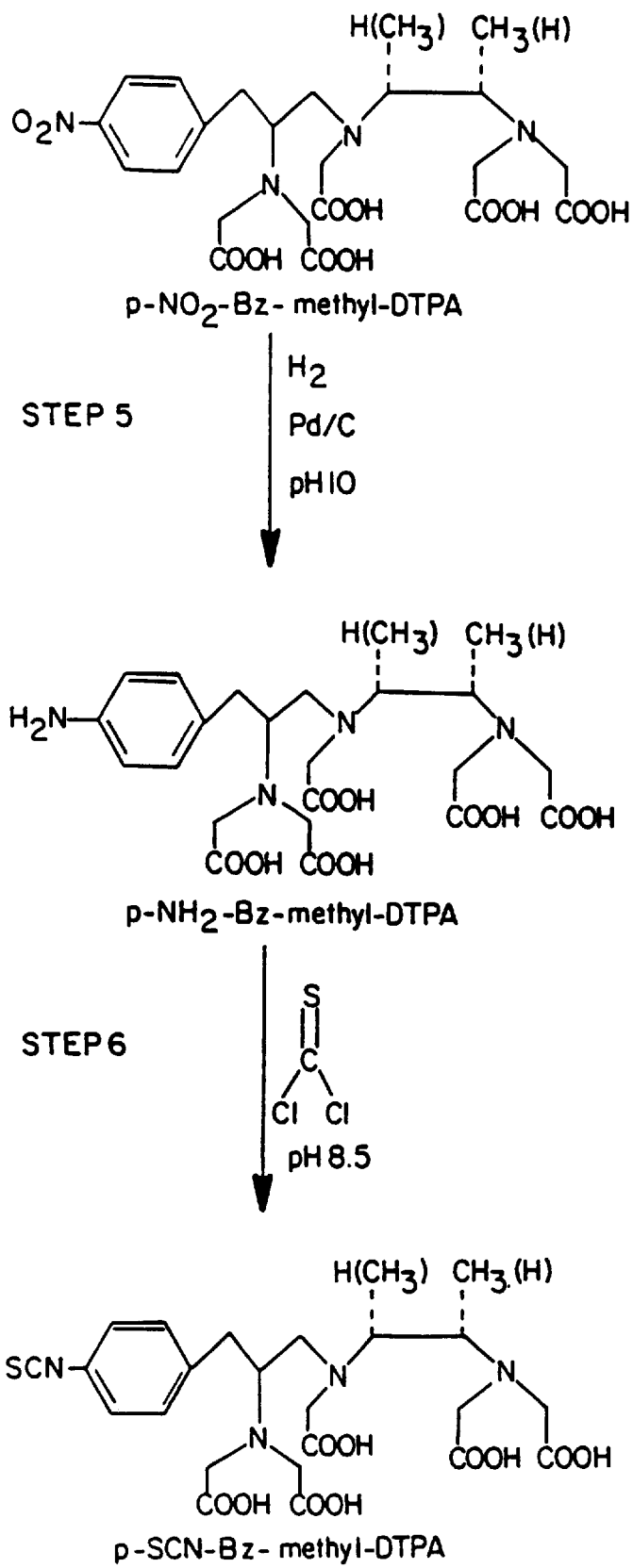

A diagrammatic representation of this synthesis is presented in FIGS. 3A–3B. This synthetic route is a modification of the procedure reported by Brechbiel et al (86) for the synthesis of 1-p-Isothiocyanato-benzylmethyl-diethylenetriaminepentaacetic acid (ITC-benzyl-DTPA). The starting material, 1-p-nitro-L-phenylalanine monohydrate is obtained from commercial sources and characterized as to identify and purity by melting point (decomposition), infrared spectroscopy, nuclear magnetic resonance, and analytical reversed phase high pressure liquid chromatography. The products are checked for identity and purity at each step by methodologies that include HPLC, infrared spectroscopy, nuclear magnetic resonance, melting point, thin-layer chromatography, fast atom bombardment mass spectroscopy and elemental analysis. The overall yield of the synthesis is quite good at about 17% (considering that it is a 6 step synthesis). The final product is filtered through a 0.22 micron sterile filter and aliquoted into sterile tubes using aseptic technique.

The aliquots of ITC-benzyl-MX are stored at −80° C. until use for conjugation with monoclonal antibody. The ITC-benzyl-MX has been shown to be stable for at least 2 years under these storage conditions. This final product is analyzed by HPLC and functional tests for purity, stability, and performance. The LAL assay for endotoxins indicates that the endotoxin concentration of this final product is less than 0.01 endotoxin units per mg of ITC-benzyl-MX.

Selection of Patients

Patient eligibility is restricted in our study to histologically or flow cytometric analysis confirmed B1 positive non-Hodgkin's lymphoma which has relapsed from conventional primary and salvage regimens. Due to the somewhat experimental nature of the therapy, patient eligibility is more restricted than we expect it to ultimately be. At the present time, patients must have a chronological age greater than 18 years. Patients must have bone marrow function that qualifies them for an autologous bone marrow transplant. Patients must be of reasonable health other than their lymphoma disease without any other malignancies, no uncontrolled viral or fungal infections, be HIV negative and have an expected survival of more than 2 months. At least three weeks must have elapsed since any prior therapy or surgery. Patients must have reasonable end organ function and hematopoiesis, including no clinically significant cardiac or pulmonary symptomology. Patients will be excluded for whom the previously received dose of radiation therapy is so great that radioimmunotherapy might exceed organ tolerances. Patients must be capable of and give informed consent before entering the study. Patients with known prior exposure or hypersensitivity to murine proteins or bone marrow transplant will be excluded. Pregnant and nursing women are excluded from the study. Patients in whom there is a failure to demonstrate localization of $^{111}$In labeled B1 in at least 50% of the known tumor sites will not receive a dose of $^{90}$Y B1.

Composition of the Drug a. Contents of Vial 1 (10 mL) and Vial 2 (3 mL)
      1. Mouse IgG2a Vial 4–6 mg/mL
         Vial 35–45 mg/mL
      2. Potassium Phosphate 1.7 mg/mL±5%
      3. Sodium Chloride 8.5 mg/mL±5%
      4. Maltose 100 mg/mL±10%

Final Product:

Coulter Clone® B1 is a clear colorless liquid in a properly labeled glass vial stoppered with a gray silicone coated butyl rubber stopper and capped with an aluminum crimp seal.

b. Contents of Vial 3 (1 mL) B1-MX-DTPA)
      1. Isothiocyanato-benzyl-methylDTPA-Mouse IgG2a 1.8–2.4 mg/mL 2. Sodium Acetate 0.05 M±5%
3. Sodium Chloride 8.5 mg/mL±5%
4. Maltose 100 mg/mL±10%

Final Product:
COULTER CLONE® B1 conjugated to Isothiocyanato-benzylmethyldiethylenetriaminepenta acetic acid is a clear colorless liquid in a properly labeled polypropylene vial stoppered with a gray teflon coated butyl rubber stopper and capped with an aluminum crimp seal.

c. Contents of Vial 4 (0.5 mL) (Acetate buffer)
1. Sodium Acetate 0.25 M±5%

Final Product:
Sterile, non-pyrogenic aqueous 0.25 M sodium acetate in a properly labeled polypropylene vial stoppered with a gray teflon coated butyl rubber stopper and capped with an aluminum crimp seal.

d. Contents of Vial 5 (1.0 mL) (Quenching Reagent)
1. EDTA 0.005 M±5%
2. Sodium Chloride 9 mg/mL±5%

Sterile, non-pyrogenic 0.005 M ethylenediamine-tetra acetate (EDTA or Versenate) in 0.9% NaCl in a properly labeled polypropylene vial stoppered with a gray teflon coated butyl rubber stopper and capped with an aluminum crimp seal.

e. Radiolabeling Agents
1. $^{111}$In in 0.04N HCl (purchased as a separate component)
$^{111}$In as cation 10 mCi/mL at assay date.

Final Preparation:
Sterile, non-pyrogenic $^{111}$In 0.04 N hydrochloric acid (Medi+Physics/Amersham Corporation product INS.1PA, or equivalent).

2. $^{90}$Y in 0.04 N HCl (purchased as a separate component) $^{90}$Y as cation 20 mCi/mL aL assay date Final Preparation: Sterile, non-pyrogenic $^{90}$Y in 0.04 N HCl (Medi+Physics/Amersham Corporation product YAS.4P, or equivalent).

The $^{111}$In-B1-MX-DTPA and $^{90}$Y-B1-MX-DTPA will be diluted with injectable 0.9% saline containing 5% human albumin (Albuminar-25, Armour Pharmaceutical Company, Kankakee, Illinois, Buminate 25%, Baxter Healthcare Corporation, Hyland Division, Glendale, Calif., or equivalent)

Dosimetry
Since dosimetry is required for $^{90}$Y, and quantitative imaging of the Bremsstahlung is extremely poor, all organ dosimetry (except the blood for which direct $^{90}$Y data will be obtained) will be derived from $^{111}$In-RIC images under the assumption that the $^{111}$In and $^{90}$Y-radiolabeled antibody posses identical pharmacokinetics.

Dosimetry protocol
1. Administer to the patient an imaging dose of $^{111}$In radioimmunoconjugate. An $^{111}$In standard will be placed at the level of the patient head for determination of the sensitivity of the camera.

2. Patient alignment relative to the table will be mated and reproduced on each imaging session.

3. Obtain anterior/posterior planar images on the whole body camera at the time points: day 1, day 2 and day 3 setting two 10% windows centered at the 245 keV and 171 keV emission energies of $^{111}$In. An additional γ-camera imaging session will be performed on day 7 following treatment with $^{90}$Y and the results will be analyzed for the $^{111}$In, and if possible $^{90}$Y, distribution.

4. Draw region of interest (ROI) around tumor regions, heart, liver, spleen, lung and muscle (background). RC)I will be correlated with normal organs and known tumor volumes from CT scans.

5. Take geometric mean of total pixel count divided by number of pixels in ROI from opposed views, so that one has a value for the average cpm/pixel for each organ. This value is almost independent of the depth of the source within the patient, but is dependent on the patient thickness. Patient separation will be measured at head, neck, chest, abdomen, hips and legs.

6. The geometric mean of the cpm/pixel from each ROI will be converted to an activity of $^{111}$In following calibration of the machine using a set of standard specific activity sources of different volume measured within a water phantom for varying water depths in the tank. The intention of this study is to obtain a relation between mean cpm/pixel and μci/g for $^{111}$In, as well as a set of attenuation values for several water depths.

7. Obtain the average cpm/pixel for the whole body derived rom images of the head, chest, abdomen, pelvis and legs on day 1. This data will be related to total activity of $^{111}$In administered and is a consistency check with the phantom data.

8. The geometric mean of the total cpm for whole body and each tissue of interest will be converted to $^{111}$In μCi/g. The conversion of cpm to activity is given by the formula given below.

$$A = SQRT(I_a \cdot I_p) * 1/[k * \exp(-\mu T/2)]$$

where $I_a$ and $I_p$ are the cpm/pixel from anterior and posterior counts respectively, $\mu T/2$ is the attenuation half thickness for the double indium peak and will be derived from the water phantom studies described in step 6, and k is a camera sensitivity conversion factor of the cpm/pixel per μCi/g in air obtained from step 1.

9. For each set of images cpm/ROI will be converted to μCi/g in that tissue. Each set of data will then be decay corrected to yield the biological uptake and clearance curve Y for each tissue.

10. The decay corrected data for each ROI will be plotted and fitted to an exponential clearance curve $Y(t) = a\exp(-\lambda_{b1} t)$ or an exponential accretion and clearance $Y(t) = a(1 - \exp(-\lambda_{b2} t)) \cdot \exp(-\lambda_{b1} t)$, where Y(t) is the tissue retention as a function of time, $\lambda_{b1}$ and $\lambda_{b2}$ are biological clearance and accretion constants, and a is a constant reflecting the peak fractional uptake in the tissue of interest.

11. The dose calculation for each tissue will be performed using the MIRD (Medical Internal Radiation Dose Committee) protocol. The radiation absorbed dose D is given by $$D = (1/m) A(t) \cdot Y(t) dt \cdot \Sigma \Delta_i \phi_i$$

where A(t) is the physical decay curve for $^{90}$%, Y(t), the retention characteristics, m, the organ mass and $\Sigma \Delta_i \phi_i$, the equilibrium dose constant for the radionuclide. For $^{90}$Y $\Sigma \Delta \phi_i = 1.984$ (g) (cGy)/(μci) (hr). Since $^{90}$Y is a pure β$^-$-emitter, and the yield of Bremsstrahlung low, all the emitted radiation can be assumed to be non-penetrating, i.e. deposited within the organ containing that activity. Extrapolation of the biological and physical clearance rates for normal organs will be assumed to parallel that of the blood.

12. Patients blood will be sampled 20 minutes after administration of the $^{111}$In and $^{90}$Y radiolabeled antibody and then daily thereafter. Pharmacokinetics and absorbed dose calculations for blood will be determined from direct measurements of the specific activity of $^{90}$Y from aliquots of the patients blood in a well scintillation counter. Comparison of the clearance curves for $^{111}$In and $^{90}$Y from the blood will be a good indicator of the relative stability of the two RICs. Appropriate detection procedures will be used to obtain independent $^{90}$Y and $^{111}$In information from the blood specimens. Alternative methods of calculating dosimetry estimates are within the scope of general knowledge.

Radioimmunoscintigraphy and Radioimmunotherapy of Patients Using Anti-B1 Antibody In this study unlabeled B1 (2.5 mg/kg) is administered to patients 1 hour before the administration of the radiolabeled B1 to minimize the non-specific organ uptake of the radiolabeled B1. Antibody chelated with 5 millicuries of $^{111}$In per dose or 20, 30, 40, or 50 mCi $^{90}$Y (or 5 mCi intervals as the dose nears the maximum tolerated dose) is administered on B1-MX-DTPA (1 to 10 mg) mixed with unlabeled B1 for a total dose of 10 mg of antibody administered by intravenous infusion.

1. $^{111}$In-B1 and $^{90}$Y-B1 Studies of Patient BLE

The urinary excretion of $^{111}$In was only 7.47% of total dose at 63 hours with no unlabeled B1 carrier, but increased to 13.85% of total dose with a 1 mg/kg B1 dose. The estimated radiation dose from $^{111}$In was higher for liver (1.22 cGy/mCi $^{111}$In or extrapolated 10.77 cGy/mCi $^{90}$Y) with 2 mg $^{111}$In-B1-MX only than the estimated radiation dose for liver (0.62 cGy/mCi $^{111}$In or extrapolated 5.86 cGy/mCi $^{90}$Y) when 1 mg/kg of carrier B1 was given (see TABLE 7). The dose estimates for the other organs were similar at both doses of B1. Carrier B1 (1 mg/kg) was selected as the dosage for administration with the therapeutic dose of $^{90}$Y B1-MX-DTPA.

Only a minor transient decrease in platelet concentration (nadir 113,000 platelets/$\mu$L) was detected about 4 weeks after the administration of 20 mCi $^{90}$Y-B1-MX-DTPA (see TABLE 8). There were no remarkable changes in other hematologic parameters for this patient after treatment (except: that WBC decreased slightly from the 4000 to 7000/uL range pre-treatment to 3700 to 4800/$\mu$L range during the 4 weeks after treatment (TABLE 8). It was not necessary to re-infuse the patient's harvested autologous stem cells. The patient experienced light-headedness upon standing without loss of consciousness for a three day period, occurring about 2 months after treatment.

The follow-up examinations of BLE one month after treatment with $^{90}$Y-B1-MX-DTPA indicated a minor response in para-aortic and pelvic lymph nodes, but the right inferior gluteal node was estimated at 5.1×3.1×3.6 cm by doppler flow. Follow-up at 2 months, 3 months, and 5 months has indicated stable disease (right inferior gluteal node was estimated at 4.4×3.2×4.4 cm by doppler flow after 5 months), but no further decrease in disease has been noted.

2. $^{111}$In-B1 and $^{90}$Y-B1 Studies of Patient FPD

FPD entered on study after it was determined that he remained HAMA negative despite prior exposure to murine monoclonal antibodies. Prior to imaging with $^{111}$In-B1-MX-DTPA left axillary node was 1.5 cm by palpation with no abdominal abnormalities detectable by CT. The para-aortic node at L4 was 1.0×0.8 cm by CT. The left Axillary node imaged by radioimmunoscintigraphy with $^{111}$In-B1-MX-DTPA at the no carrier B1 dose and 1 mg/kg dose (83 mg B1). In addition a nodular pattern of uptake in the spleen that may be lymphoma was detected with $^{111}$In-B1-MX-DTPA (first dose 2 mg $^{111}$In-B1-MX, second dose 1 mg/kg B1 or 83 mg B1 plus 2 mg $^{111}$In-B1-MX).

The urinary excretion of $^{111}$In was 14.14% of total dose at 70 hours with no unlabeled B1 carrier and 13.550% at 71.9 hours with a total dose with a 1 mg/kg B1. The blood pool $^{111}$In was only 8.83% of the total dose at 70.5 hours when no carrier B1was given, but was 36.47% of the total dose when 1 mg/kg was given. The estimated radiation dose from $^{111}$In was higher for spleen (0.08 cGy/mCi $^{111}$In or extrapolated 0.74 cGy/mCi $^{90}$Y) with 2 mg $^{111}$In-B1-MX only than the estimated radiation dose for spleen (0.14 cGy/mCi $^{111}$In or extrapolated 1.36 cGy/mCi $^{90}$Y) when 1 mg/kg of carrier B1 was given (see TABLE 7). This increase in the radiation dose to total body is due to the increased fraction of $^{111}$In-B1 in blood pool with time. The use of no carrier B1 lowered the background radiation to normal organs. FPD was given 20 mCi of $^{90}$Y-B1 (2 mg B1-MX-DTPA) without carrier B1.

No significant decrease in platelet concentration has been detected in this patient post-treatment. There were no remarkable changes in other hematologic parameters for this patient. It was not necessary to re-infuse the patient's harvested autologous stem cells. The patient experienced no acute or chronic adverse reactions to the therapy.

The follow-up examinations of FPD one month and two months after treatment with $^{90}$Y-B1-MX-DTPA indicate partial responses at both times. After one month no palpable axillary nodes were found and the para-aortic node at L4 was 0.5×0.4 cm by CT. After two months no palpable axillary disease was detected and the para-aortic node was less than 0.3×0.3 cm by CT.

3. $^{111}$In-B1 and $^{90}$Y-B1 Studies of Patient NWM

For patient NWM, prior to imaging with $^{111}$In-B1-MX-DTPA, left axillary node was 1.5 to 2.0 cm by palpation with extensive abdominal abnormalities detectable by CT. Bilateral inguinal adenopathy was detected. Small (less than 1 cm) nodes in the gastrohepatic ligament, iliac region, pancreatic, para-aortic chains were detected. Mediastinal and bilateral axillary nodes were also positive. Radioimmunoscintigraphy with $^{111}$In-B1-MX-DTPA at the no carrier B1 dose revealed localization in the mediastinal, left axillary and mesenteric (para-pancreatic) nodes. Imaging after $^{111}$In-B1-MX-DTPA plus the 1 mg/kg carrier dose of B1(106 mg) resulted in significant improvement in the number of nodes that imaged. The carrier dose allowed images of the left supraclavicular, right and left Infraclavicular, mediastinal, left hilar, right and left axillary, para-aortic, mesenteric, right and left external iliac and right and left inguinal nodes.

The urinary excretion of $^{111}$In was 18.03% of total dose at 72 hours with no unlabeled B1 carrier and 36.08% at 71.2 hours with a total dose with a 1 mg/kg B1. The blood pool $^{111}$In was only 4.54% of the total dose at 72.5 hours when no carrier B1 was given, but was 24.41% of the total dose when 1 mg/kg was given. The estimated radiation dose from $^{111}$In was lower for total body (0.055 Gy/mCi $^{111}$In or extrapolated 0.53 cGy/mCi $^{90}$Y) with 2 mg $^{111}$In-B1-MX only than the estimated radiation dose for total body (0.092 cGy/mCi $^{111}$In or extrapolated 0.88 cGy/mCi $^{90}$Y) when 1 mg/kg of carrier B1was given (see TABLE 7). This increase in the radiation dose to total body is due to the increased fraction of $^{111}$In-B1 in blood pool with time. The use of carrier B1 improved the targeting of lymph node sites of disease and increased the urinary clearance of $^{111}$In. NWM was given 20 mCi of $^{90}$Y-B1 (2 mg B1-MX-DTPA) with 1 mg/kg (108 mg) of carrier B1.

4. $^{111}$In-B1 and $^{90}$Y-B1 Studies of Patient JEF

For JEF, bone marrow involvement with tumor was estimated at 10% of intra-trabecular space with 20% fat. Extensive abdominal nodal involvement including the retrocrural, right and left para-aortic, mesenteric, and right and left common, internal and external iliac nodes. The largest (left) para-aortic node measured 6.5×5 cm and the retrocrural and mesenteric nodes were <2 cm by CT. The spleen was slightly enlarged. Imaging with $^{111}$In-B1-MX-DTPA (2.5 mg/kg B1 antibody) resulted in an excellent correlation between the radioimmunoscintographs and the concomitant CT scan. The B1antibody scan agreed with the known sites of disease. Bone marrow also showed positive on the scan.

JEF received 20.25 mCi of $^{90}$Y-B1-MX-DTPA with 2 mg/kg B1 monoclonal antibody (153 mg B1). JEF experienced no adverse reaction to either dose of el monoclonal antibody. The $^{90}$Y cleared from the blood at a rate consistent with a blood half-life of 25.5 hours. The calculated dosimetry estimates estimated that the spleen received a radiation dose of 42.47 cGy/mCi $^{90}$Y-B1-MX-DTPA (TABLE 7). Liver and left kidney were estimated to receive 22.47 cCy/mCi $^{90}$Y. The bone marrow was estimated to receive 4.49 cGy/mCi $^{90}$Y based upon a single point bone biopsy.

Autologous bone marrow was re-infused into JEF 18 days after the close of $^{90}$Y-B1-MX-DTPA. Twenty-four days after treatment with $^{90}$Y-B1-MX-DTPA the patient was judged to have had a minor response with some decrease in splenomeglia and the left para-aortic node had decreased from 6.5×5 cm to 5.5×4.5 cm measured by CT. Restaging of the patient 57 days after treatment indicated a further minor response with the L para-aortic node decreasing to 4×5 cm. Re-staging at 86 days indicated no further reduction in disease, but stable disease (left para-aortic node 3.5×4.8 cm). This patient had progressive disease prior to treatment with $^{90}$Y-B1.

JEF experienced a grade III decrease in platelet counts of approximately 31 days duration. The observed nadir of 26,000 platelets/μL was at day 24 after treatment. JEF continued with platelet counts in the 31,000 to 54,000/μL at least through day 117 after treatment. JEF experienced no significant medical consequences to this lowered platelet levels and returned to her employment at approximately day 60 after treatment.

5. $^{111}$In-B1 and $^{90}$Y-B1 Studies of Patient BAH

Bone marrow involvement with tumor was estimated at 10of intra-trabecular space with 20% fat. Extensive abdominal nodal involvement including the retrocrural, right and left para-aortic, mesenteric, and right and left common, internal and external iliac nodes. The largest (left) para-aortic node measured 6.5×5 cm and the retrocrural and mesenteric nodes were <2 cm by CT. The spleen was slightly enlarged. Imaging with $^{111}$In-B1-MX-DTPA (2.5 mg/kg B1 antibody) resulted in good tumor localization especially in the axillary node.

BAH received 20.8 mCi of $^{90}$Y-B1-MX-DTPA with 2 mg/kg B1 monoclonal antibody (150 mg B1). BAH experience no adverse reaction to either dose of B1 monoclonal antibody. The $^{90}$Y cleared from the blood at a rate consistent with a blood half-life of 27.5 hours. The calculated dosimetry estimates estimated that the spleen received a radiation dose of 13.63 cGy/mCi $^{90}$Y-B1-MX-DTPA. Liver exposure was estimated at 16.42 cGy/mCi $^{90}$Y. The right kidney was estimated at 23.25 cGy/mCi and left kidney at 21.04 cGy/mCi $^{90}$Y. The bone marrow was estimated to receive 16.27 cGy/mCi $^{90}$Y based upon a single point bone biopsy.

Autologous bone marrow was re-infused into BAH 17 days after the dose of $^{90}$Y-B1-MX-DTPA. Twenty-three days after treatment with $^{90}$Y-B1-MX-DTPA the patient was judged to have progression of disease (especially axillary node which increased from 4×4 cm to 4.8×4.8×7 cm by CT. The hydronephrosis was stable with a slight increase in the liver lesions. Continued progression was also noted in the axillary node at 49 days (7.5×7.5 cm by CT, 10×8 cm by physical examination) with extensive pleural effusion with acute hydronephrosis and chronic hydronephrosis on the left kidney. BAH was lost to study and further interpretation. BAH developed a candida genitourinary infection secondary to the hydronephrosis. The initial interpretation was that the hydronephrosis was attributable to bulky blockage of the ureters. The patient was given 2000 cGy of external beam therapy to the abdomen, pelvis and axilla. The hydronephrosis was subsequently attributed to blockage by stones and or debris and was successfully treated.

BAH experienced a grade IV decrease in platelets with a nadir of 13,000 platelets/μL and a grade III decrease in white blood cells (1000 WBC/μL) 39 days after therapy with $^{90}$Y-B1. Because of the external beam radiation therapy it was not possible to further assess the hematological toxicity of the $^{90}$Y-B1 dose. The patient did require periodic platelet support for an extended period.

Conclusions

Significant toxicities have not been observed at the 13 and 20 mCi level of $^{90}$Y-B1-MX-DTPA. Four patients treated to date have shown 2 minor responses, one partial remission and one complete response.

Two additional patients have completed study. One additional patient that completed study had a partial response, but experienced grade III suppression of platelets. The other additional patient had a partial remission, radiotherapy was given to the brain of this patient after new disease appeared and the patient is now in a complete remission status. A third additional patient, who is thus patient number 7, received $^{90}$Y-B1-MX-DTPA therapy, but could not be evaluated for toxicity due to external beam radiation therapy that was given to treat hydronephrosis symptoms. This seventh patient's disease continued to progress, except in the field of the external beam therapy. Patient number 7 failed to demonstrate adequate tumor localization with $^{111}$In-B1-MX and thus did not enter the therapy phase of the study.

TABLE 7

Doses, radiochemical purities, imaging and toxicity for 6 patients on $^{90}$Y-B1. Patients were imaged with $^{111}$Indium-B1-MX-DTPA. A dose of B1 (2.5 mg/kg body weight at DFCI or 0 or 1 mg/kg body weight) B1 was administered just prior to administration of the imaging or therapeutic doses. Disease sites detected by radioimmunoscintigraphy/number of known sites of disease by all other methods. No adverse reactions were observed upon administration of B1/$^{111}$In-B1-MX-DTPA drug.

| Patient number | 1-001 JEF | 1-002 BAH | 1-003 SJM | 1-004 NJP | 2-001 BLE | 2-002 FPD | 2-003 NWM | 2-004 SR |
|---|---|---|---|---|---|---|---|---|
| 90-Yttrium-B1 (mCi)/mg cold B1 | 20.3 mCi 153 mg | 21.2 mCi 150 mg | No 90-Y-B1 dose | | 13.6 mCi 85 mg | 13.5 mCi | 13.7 mCi 106 mg | 21.6 mCi |
| RIS detected sites/known sites (no cold B1) | | | | | 1/10 | 2/2 | 2/9 | ? |
| RIS detected sites/known sites (with cold B1) | | | 4/4 1 unconfirmed site in lung | 0/1 | 1/10 | 2/2 | 9/9 5 unconfirmed sites** | ? |
| Clinical Response | Stabile Disease | Progression | No therapy | Partial Remission | Minor Response | Complete Remission | Partial Remission@ | Minor Response |

@Patient subsequently received radiotherapy to brain after new brain mets appeared, Patient now in complete remission
*Patient had contiguous lymphomatous involvement of the retroperitoneal and mesenteric lymphadenopathy, there was an excellent correlation with concomitant CT scan showing radiolabeled monoclonal antibody in sites of anatomically defined lymphomatous involvement. One site in knee remained unexplained.
**5 unconfirmed lymph node sites were detected by RIS.
***Chills and slight light-headedness reported during only 1 of 3 administrations of B1.

TABLE 8

Dosimetry calculations for organs total body and urinary clearance estimates from $^{90}$Y-B1 study based upon extrapolation of $^{111}$Indium-B1-MX-DTPA distribution and pharmacokinetics and clearance. Radiation dose is cGy/mCi $^{90}$Yttrium.

| Patient number | 1-001 JEF 2.5 mg/kg | 1-002 BAH 2.5 mg/kg | 2-001 BLE 0 mg B1 | 2-001 BLE 1 mg/kg | 2-002 FDP 0 mg B1 | 2-002 FPD 1 mg/kg | 2-003 NWM 0 mg B1 | 2-003 NWM 1 mg/kg |
|---|---|---|---|---|---|---|---|---|
| Total Body | 2.32 | 2.08 | 1.44 | 1.51 | 0.74 | 1.36 | 0.53 | 0.88 |
| Liver | 22.47 | 16.42 | 10.77 | 5.85 | 7.06 | 6.43 | 7.68 | 5.61 |
| Spleen | 42.47 | 13.63 | 4.84 | 4.27 | 17.23 | 7.41 | 10.76 | 11.28 |
| Heart | 12.79 | 18.54 | 11.82 | 12.75 | 6.14 | 8.41 | 1.73 | 5.47 |
| Right Kidney | 14.47 | 23.25 | | | | | | |
| Left Kidney | 22.47 | 21.04 | | | | | | |
| Lumbar Spine | | | 2.94 | 3.62 | | | | |
| Lung | 14.32 | 8.63 | | | | | | |
| Bone Marrow (biopsy) | 4.49 | 16.27 | | | | | | |
| Blood | 6.96 | 8.07 | | | | | | |
| Blood Biol T1/2 90-Y (hrs) | 25.5 | 27.5 | | | | | | |
| Urinary excretion 111 In (% TD) | | | 7.5% TD at 63 hr | 13.9% TD at 63 hr | 14.1% TD at 70 hr | 13.6% TD at 72 hr | 18.0% TD at 72 hr | 36.1% TD at 72 hr |
| Urinary excretion 90-Y (% TD) | | | | 12.2% TD at 87 hr | 9.2% TD at 59 hr | | | 16.1% TD at 71 hr |

EXAMPLE IV

SENSITIZATION OF LYMPHOMA CELLS BY ANTI-CD20 ANTIBODY

Apoptosis is a phenomenon in cell biology, wherein a cell becomes committed to its own destruction. A cell which is apoptotic displays characteristic changes in metabolism, which ultimately result in fragmentation of cellular DNA and lysis of the cell.

The excellent results described above for radioimmunotherapy using an anti-CD20 antibody might be due, in part, to synergism in the induction of apoptosis by binding of the anti-CD20 antibody and the irradiation of the tumor cell. The evidence for this hypothesis comes primarily from the tumor responses observed to the trace-labeled antibody administered for imaging purposes.

Given such synergism in the induction of apoptosis by binding of unlabeled anti-CD20 and some second insult to the cell, it is expected that administration of an anti-CD20 antibody could be combined with a variety of secondary treatments to achieve the same synergism. For example, binding of a second antibody, directed against a different antigen than CD20, that is conjugated to a radionuclide would provide the same synergistic second insult to the tumor cell as is provided by an anti-CD20 radioimmunoconjugate.

Also, a similar effect could be provided by external beam irradiation. If external beam irradiation is used, then the dose to be administered should be in the range of 100 to 250 cGy to whole body if bone marrow replacement support is not contemplated. However, if bone marrow replacement is used as an adjunct therapy, doses as high as 1000 cGy to whole body could be used. Such a large dose would likely be administered in a series of fractional doses.

Finally, one can consider inducing the apoptosis events synergistically by administering a chemotherapeutic agent. In choosing the chemotherapeutic agent, one would preferably employ a drug which is a DNA alkylating agent, such as cyclophosphamide or chlorambucil. Another preferred class of drugs are the antimetabolites, such as methotrexate. In particular, cyclophosphamide, chlorambucil, doxorubicin and methotrexate are preferred to be administered for this mode of therapy.

REFERENCES

The following articles from the scientific and/or patent literature are cited in the present disclosure. Each of the articles is hereby incorporated, in its entirety, by such citation.

1. P. Klimo, Chemotherapy for aggressive non-Hodgkin's lymphomas, In DeVita VT, Hellman S, Rosenberg SA (eds): Cacner: Principles and Practice of Oncology—Update 2 (no. 9), Philadelphia, Lippincott, 1988, pp. 1–12.
2. F. Applebaum et al, J. Clin. Oncol. 5:1340 (1987).
3. A. J. McMichael, Leukocyte Typing III, pp. 302–363 and 432–469, Oxford, England, Oxford University Press, 1987.
4. R. A. Miller et al, New Eng. J. Med. 306:517 (1982).
5. T. C. Meeker et al, Blood 65:1349 (1985).
6. T. Meeker et al, N. Eng. J. Med. 312:1658 (19850).
7. I. Royston et al, J. Immunol. 125:725 (1980).
8. K. A. Foon et al, Blood 64:1085 (1984).
9. R. A. Miller et al, Blood 58:78 (1981).
10. R. A. Miller et al, Blood 62:988 (1983).
11. R. O. Dillman et al, Blood 59:1036 (1982).
12. P. Stashenko et al, J. Immunol. 125:1678 (1980).
13. L. M. Nadler et al, J. Immunol. 126:1941 (1981).
14. D. A. Brooks et al, Clin. Exp. Immunol. 39:477 (1980).
15. D. A. Brooks et al, J. Immunol. 126:1373 (1981).
16. L. M. Nadler et al, J. Immunol. 131:244 (1983).
17. C. Abramson et al, J. Immunol. 126:83 (1981).
18. R. C. Ash et al, Blood 60:1310 (1982).
19. J. Ritz et al, Nature 283:583 (1980).
20. R. C. Bast et al, Cancer Res. 43:1389 (1983).
21. J. Ritz et al, Lancet 2:60 (1982)
22. N. K. C. Ramsay et al, Blood 62:228a (abstr) (1983).
23. O. W. Press et al, Blood 69:584 (1987).
24. P. A. Bunn et al, Lancet 2:1219 (1984).
25. C. C. Badger et al, Cancer Res. 45:1536 (1985).
26. S. Rosen et al, J. Clin. Oncol. 5:562 (1987).
27. D. J. Buchsbaum, Cancer Res. 48:2475 (1988).
28. S. DeNardo, Antibod. Immunoconjugates Radiopharmaceut. 1:17 (1988).
29. A. L. Epstein et al, Cancer Res. 47:830 (1987).
30. M. Link et al, J. Immunol. 137:3013 (1986).
31. O. W. Press et al, J. Clin. Oncol. 7:1027 (1989).
32. T. F. Tedder et al, J. Immunol. 135:974 (1985).
33. T. F. Tedder et al, Eru J. Immunol. 16:881 (1986E).
34. J. T. Golay et al, Immunology 62:279 (1987).
35. J. T. Golay et al, J. Immunol. 135:3795 (1985).
36. E. A. Clark et al, Proc. Natl. Acad. Sci. USA 82:1766 (1985).
37. A. Forsgren et al, Regulation of B cell function through the CD20 (B1) molecule. In Leucocyte Typing III: White Cell Differentiation Antigens. A. J. McMichael et al, eds. Oxford University Press, Oxford, p. 396.
38. N. L. Lelvin et al, Nucl. Med. Biol. 14:99 (1987)
39. The Non-Hodgkin's Lymphoma Pathologic Classification Project Writing Committee: National Cancer Institute sponsored study of classifications of non-Hodgkin's lymphomas, Cancer 49:2112 (1982).
40. A. S. Freedman et al., J. Clin. Oncol. 8:784 (1990).
41. L. I. Gordon et al, N. Engl. J. Med., 327:1342 (1992).
42. R. I. Fisher, N. Engl. J. Med., 328:1002 (1993).
43. J. O. Armitage, Blood, 73:1749 (1989).
44. V. T. DeVita, Jr. et al, Cancer: principles and practice of oncology, 3rd ed. Vol. 2, Philadelphia: J. B. Lippincott, pp. 1741 (1989).
45. P. J. Fraker et al, Biochem. Biophys. Res. Commun., 80:849 (1978).
46. R. L. Wahl et al, J. Nucl. Med., 31:84 (1990).
47. T. Lindmo et al, J. Immunol. Methods, 72:77 (1984).
48. D. Y. Mason et al, Am J. Pathol., 136:1215 (1990).
49. M. S. Kaminski et al, J. Clin. Oncol., 10:1696 (1992).
50. International Commission on Radiological Protection. Report of the Task Group on Reference Man. Oxford, England: Pergamon Press, 1975.
51. W. H. Ellet et al, NM/MIRD pamphlet no. 8, New York: Society of Nuclear Medicine.
52. L. T. Dillman et al, NM/MIRD pamphlet no. 10, New York: Society of Nuclear Medicine.
53. W. S. Snyder et al, NM/MIRD pamphlet no. 11, New York: Society of Nuclear Medicine.
54. E. Watson et al, MIRDOSE, 2nd ed., Oak Ridge, Tenn.: Associated Universities, 1984.
55. L. M. Nadler et al, Cancer Res., 40:147 (1980).
56. S. L. Brown et al, Blood, 73:651 (1989).
57. G. T. Stevenson et al, Int. J. Cancer Suppl., 3:9 (1988).
58. G. Hale et al, Lancet, 2:1394 (1988).
59. M. J. S. Dyer et al, Blood, 73:1431 (1989).
60. E. S. Vitetta et al, Cancer Res., 51:4052 (1991).
61. M. L. (Grossbard et al, Blood, 79:576 (1992).
62. M. L. Grossbard et al, J. Clin. Oncol., 11:726 (1993).
63. D. M. Goldberg et al, J. Clin. Oncol., 9:548 (1991).
64. S. J. DeNardo et al, Int. J. Cancer Suppl., 3:96 (1988).
65. G. L. DeNardo et al, Cancer Res., 50:Suppl:1014S (1990).
66. D. A. Scheinberg et al, J. Clin. Oncol., 8:792 (1990).
67. O. W. Press et al, Cancer Res., 49:4906 (1989).
68. B. W. Wessels et al, Int. J. Radiat. Oncol. Biol. Phys., 17:1257 (1989).
69. D. J. Buchsbaum et al, Int. J. Radiat. Oncol. Biol. Phys., 18:1033 (1990).

70. S. J. Knox et al, Cancer Res., 50:4935 (1990).
71. R. M. Macklis et al, Radiat. Res., 130:220 (1992).
72. R. M. Macklis et al, Antibodies Immunoconjugates Radiopharm., 5:339. abstract (1992).
73. D. J. Buchsbaum et al, Cancer Res., 52:6476 (1992).
74. Nadler, L. M., Lymphocyte Typing II, Vol. 2 pp. 3–37 and Appendix, E.L. Renling, et al. eds., c. 1986 by Springer Verlag.
75. Nadler, L. M. et al. "*Cellular Origins of Human Leukemias and Lymphomas*", in *Leukemia Markers* pp. 3–17, W. Knapp, ed.; c. 1981 by Academic Press, Inc., New York, N.Y.
76. M. Magerstadt, *Antibody Conjugates and Malignant Disease*, pp. 93–109; c 1991 by CRC Press, Boca Raton, Fla.
77. R. Stein et al., Br. J. Haematol. 80:69 (1992).
78. R. M. Macklis et al., Abstracts of the Fourth Conference on Radioimmunodetection and Radioimmunotherapy of Cancer, Princeton, N.J., 1992.
79. J. A. Siegel et al., Med. Phys. 20(pt. 2):579 (1993).
80. P. Stashenko et al., Proc. Natl. Acad. Sci. USA 78:6 3848 (1981).
81. A. K. Bhan et al., J. Exp. Med. 57:1105 (1981).
82. H. C. Oettgen et al., Hybridoma 2:17 (1982).
83. L. M. Nadler et al., J. Clin. Invest. 74:332 (1984).
84. L. M. Nadler et al., Lancet II:427 (1982).
85. J. M. Lipton et al., Blood 60 (Suppl. 1):170 (abstract) (1982).
86. J. S. Greenberger et al., Cancer Res. 45:758 (1985).
87. F. C. Greenwood and W.M. Hunter, Biochemistry Journal 89:114 (1963).
88. Dörken et al., *Leucocyte Typing IV: White Cell Differentiation Antigens*, W. Knapp et al., eds., pp, 34–35.
89. T. F. Tedder et al., Id. pp. 36–38.
90. A. Pezzutto et al., Id. pp. 39–40.
91. J. G. Shields et al., Id. pp. 40–42.
92. F. Kiesel et al., Leukemia Research II, 12:1119 (1987).
93. M. W. Brechbiel et al., Inorganic Chemistry, 25:2772 (1986).
94. L. M. Nadler et al., in *Progress in Hematology, Vol. XII*, pp. 187–206, E. B. Brown, ed., c. 1981 by Grune & Stratton, Inc.

What is claimed is:

1. A composition comprising:
(1) a radioactively labelled monoclonal antibody or radioactively labelled monoclonal antibody fragment in an amount providing 1 to 200 mCi of radioactivity and providing irradiation in a dose range of 10 to 200 cGy to the whole body of a human patient, said amount being effective for achieving remission of B-cell lymphoma in the patient, wherein said antibody or said antibody fragment binds to CD20 antigen present on the surface of cells of B-cell lymphoma and wherein the amount of radioactivity that labels the antibody or antibody fragment is less than the amount which causes myelosuppression severe enough to require the reintroduction of hematopoietic stem cells into said patient in order for the patient to recover hematopoietic function, and
(2) a pharmaceutically acceptable carrier.

2. The composition of claim 1, wherein the radioactively labelled monoclonal antibody or radioactively labelled monoclonal antibody fragment is labelled with a β-emitter.

3. The composition of claim 2, wherein the radioactively labelled monoclonal antibody or radioactively labelled monoclonal antibody fragment is labelled with an isotope selected from the group consisting of $^{131}$I, $^{90}$Y, $^{188}$Re, and $^{186}$Re.

4. The composition of claim 1, wherein the amount of the radioactively labelled monoclonal antibody or radioactively labelled monoclonal antibody fragment provides irradiation in a dose range of 15 to 150 cGy to the whole body of the patient.

5. The composition of claim 4, wherein the amount of the radioactively labelled monoclonal antibody or radioactively labelled monoclonal antibody fragment provides irradiation in a dose range of 25 to 100 cGy to the whole body of the patient.

6. The composition of claim 5, wherein the amount of the radioactively labelled monoclonal antibody or radioactively labelled monoclonal antibody fragment provides an irradiation dose of 75 cGy to the whole body of the patient.

7. The composition of claim 1, wherein the amount of the radioactively labelled monoclonal antibody or radioactively labelled monoclonal antibody fragment is an amount providing 1 to 150 mCi of radioactivity.

8. The composition of claim 7, wherein the amount of the radioactively labelled monoclonal antibody or radioactively labelled monoclonal antibody fragment is an amount providing 1 to 100 mCi of radioactivity.

9. The composition of claim 3, wherein the isotope is $^{131}$I.

10. The composition of claim 3, wherein the isotope is $^{90}$Y.

11. The composition of claim 1, wherein the radioactively labeled monoclonal antibody or radioactively labeled monoclonal antibody fragment has a specific activity in a range of 1 to 10 mCi/mg.

12. The composition of claim 1 wherein the amount of the radioactively labeled monoclonal antibody or radioactively labeled monoclonal antibody fragment has sufficient affinity and specific activity to deliver 10.6+/−2.76 cGy/mCi to a tumor targeted by the antibody or antibody fragment when administered to a patient.

* * * * *

UNITED STATES PATENT AND TRADEMARK OFFICE
CERTIFICATE OF CORRECTION

Patent No.: 6,015,542

Dated: January 18, 2000

Inventor(s): Mark S. Kaminski, et al.

It is certified that error appears in the above-identified patent and that said Letters Patent is hereby corrected as shown.

On the face of the patent, under the section entitled "Related U.S. Application Data," delete "08/121,282" and replace with --08/121,582--.

At column 6, line 27, delete "shows" and replace with --show--.

At column 17, line 30, delete "(FIG. 1)" and replace with --(FIGS. 1A-1B)--.

Signed and Sealed this

Seventeenth Day of April, 2001

Attest:

NICHOLAS P. GODICI

Attesting Officer

Acting Director of the United States Patent and Trademark Office